US010912299B2

(12) United States Patent
Herdt et al.

(10) Patent No.: US 10,912,299 B2
(45) Date of Patent: Feb. 9, 2021

(54) WEAR RESISTANT ANTIMICROBIAL COMPOSITIONS AND METHODS OF USE

(71) Applicant: Ecolab USA Inc., Saint Paul, MN (US)

(72) Inventors: Brandon Herdt, Hastings, MN (US); Richard Staub, Jr., Lakeville, MN (US); Kevin Tauer, Eagan, MN (US); Kim R. Solomon, Woodbury, MN (US)

(73) Assignee: Ecolab USA Inc., Saint Paul, MN (US)

( * ) Notice: Subject to any disclaimer, the term of this patent is extended or adjusted under 35 U.S.C. 154(b) by 224 days.

(21) Appl. No.: 14/864,437

(22) Filed: Sep. 24, 2015

(65) Prior Publication Data
US 2016/0058012 A1 Mar. 3, 2016

Related U.S. Application Data

(63) Continuation of application No. 13/314,264, filed on Dec. 8, 2011, now abandoned.

(60) Provisional application No. 61/422,908, filed on Dec. 14, 2010.

(51) Int. Cl.
| A01N 47/44 | (2006.01) |
| A01N 33/12 | (2006.01) |
| C09D 5/14 | (2006.01) |
| A01N 25/02 | (2006.01) |
| A01N 25/24 | (2006.01) |
| A01N 59/00 | (2006.01) |

(52) U.S. Cl.
CPC ............ *A01N 47/44* (2013.01); *A01N 25/02* (2013.01); *A01N 25/24* (2013.01); *A01N 33/12* (2013.01); *A01N 59/00* (2013.01); *C09D 5/14* (2013.01)

(58) Field of Classification Search
None
See application file for complete search history.

(56) References Cited

U.S. PATENT DOCUMENTS

| 4,999,386 A | 3/1991 | Oakes et al. |
| 5,154,920 A | 10/1992 | Flesher et al. |
| 5,585,407 A | 12/1996 | Patel et al. |
| 6,087,400 A | 7/2000 | Dyer et al. |
| 6,180,584 B1 | 1/2001 | Sawan et al. |
| 6,303,557 B1 | 10/2001 | Colclough |
| 7,030,163 B2 | 4/2006 | Duneas |
| 7,488,757 B2 | 2/2009 | Hoang et al. |
| 8,007,834 B2 | 8/2011 | Collin et al. |
| 2002/0022660 A1 | 2/2002 | Jampani et al. |
| 2002/0183233 A1* | 12/2002 | Mitra ............... C11D 1/62 510/438 |
| 2003/0096722 A1 | 5/2003 | Caselli et al. |
| 2007/0059332 A1 | 3/2007 | Graham et al. |
| 2008/0319070 A1 | 12/2008 | Kany et al. |
| 2009/0155451 A1 | 6/2009 | Ylitalo et al. |
| 2009/0246165 A1 | 10/2009 | Toreki et al. |
| 2010/0240762 A1 | 9/2010 | McGeechan et al. |

FOREIGN PATENT DOCUMENTS

| EP | 0041448 A1 | 12/1981 |
| EP | 0099209 A1 | 1/1984 |
| WO | 2001023510 A2 | 4/2001 |
| WO | 2001041567 A1 | 6/2001 |
| WO | 2002077149 A2 | 10/2002 |
| WO | 2003061610 A1 | 7/2003 |
| WO | 2005097960 A1 | 10/2005 |
| WO | 2009010749 A2 | 1/2009 |
| WO | 2009037445 A1 | 3/2009 |
| WO | 2010043863 A2 | 4/2010 |
| WO | 2010097639 A2 | 9/2010 |

OTHER PUBLICATIONS

International Searching Authority, "International Search Report" issued in connection to International Application No. PCT/IB2011/055555, 9 pages, dated Sep. 26, 2012.

* cited by examiner

*Primary Examiner* — Melissa L Fisher
(74) *Attorney, Agent, or Firm* — McKee, Voorhees & Sease, PLC

(57) ABSTRACT

Anti-microbial compositions comprising (a) a quaternary ammonium compound and (b) a cationic biocide. Applicant has discovered a synergistic combination of the two components with the ration of cationic biocide to quaternary ammonium being less than 1:10 or with a single quaternary compound in a ratio of less than 1.6 to 1 provide a film forming coating that has residual anti-bacterial activity and improved durability with strong resistance to general wear between applications.

6 Claims, No Drawings

WEAR RESISTANT ANTIMICROBIAL COMPOSITIONS AND METHODS OF USE

CROSS-REFERENCE TO RELATED APPLICATIONS

This application claims priority under 35 U.S.C. § 119 to application Ser. No. 13/314,264 filed Dec. 8, 2011, which claims the benefit of provisional Application Ser. No. 61/422,908 filed Dec. 14, 2010, both of which are herein incorporated by reference in their entireties.

FIELD OF THE INVENTION

This invention relates to anti-microbial compositions and use of the same to disinfect or clean various surfaces.

BACKGROUND OF THE INVENTION

Microbes may often be present on many common objects and surfaces in everyday life. Microbes can include, for example, bacteria, fungi, spores, viruses, prions, microorganisms such as, e.g., *Mycobacterium tuberculosis, Listeria monocytogenas, Escherichia coli, Pseudomonas aeruginosa, Salmonella typhimurium, Salmonella enteritidis, Legionella* bacteria, *Yersinia pestis, Staphylococcus aereus, Bacillus subtilis, Enterobacter aerogenes, Streptococcus faecalis, Legionella pneumophila, Vibrio parahaemolyticus, Bacillus cereus*, and other gram positive and gram negative microorganisms. Several such microbes/microorganisms, individually or in combination, can cause illness or other health problems, for example, when they come into contact with humans and/or animals, or when they are ingested along with food which has contacted them.

These microbes present health hazards due to infection or contamination. When microorganisms are present on the surface of a substrate they can replicate rapidly to form colonies. The microbial colonies form a coating on the substrate surface, which is known as a biofilm. Biofilms frequently consist of a number of different species of microorganisms which in turn can be more difficult to eradicate and thus more hazardous to health than individual microorganisms. Some microorganisms also produce polysaccharide coatings, which makes them more difficult to destroy. The microorganisms attach themselves to substrates forming a biofilm comprising a "calyx" of polysaccharides and/or similar natural polymers as the affixing mechanism. Without this affixing point, the reproduction of the microorganism particularly bacteria cannot proceed, or is at least seriously impaired.

The health care and medical industry has an acute need for micro-organism-resistant surfaces. For example, hospitals and other medical facilities may have a particular need for sterile and uncontaminated surfaces, both in surgical areas as well as in convalescence facilities, where patient exposure may be significant and resistance to such microbes may be lowered. Much time and effort can be spent, for example, on sterilizing medical instruments, testing devices, etc. Often, such devices can be provided with disposable components or covers (e.g., disposable thermometer probes) to avoid cross-contamination between patients. Disposable needles are also commonly used. Such disposable materials involve increased costs and increased waste, as well as potential safety issues associated with their disposal.

The food-preparation and delivery industry is another area in which presence of microbes (e.g., bacteria) can be problematic. Food preparation facilities, if contaminated with microbes, can lead to contamination of food which may cause health problems when ingested. For example, restaurants, food manufacturing plants, and even home kitchens can contain preparation surfaces, utensils, and equipment which may contaminate food that comes into contact with them. There may be, for example, a particular need for reducing a presence and spreading of microbes in meat packaging plants.

Public and private facilities such as, e.g., restrooms, may also contain surfaces which can harbor and spread microbes, leading to potential health problems. To address this issue, products such as antimicrobial soaps and air dryers for hands may be offered, as well as disposable paper towels. Nevertheless, microbes may still be harbored on such objects as faucet and toilet handles, door knobs, keys, dispenser levers, etc.

In the transportation industry, including land, sea, air, and space vehicles, there may also be particular surfaces which can harbor and spread microbes, leading to potential health problems. For example, rental cars may benefit from durable antimicrobial surfaces (both interior and exterior). In particular, isolated environments such as, e.g., airplanes and submarines can also be safer if provided with antimicrobial surfaces.

Other common objects may benefit from antimicrobial compositions, which can inhibit or prevent spread of microorganisms between people and/or animals that come into contact with such objects. For example, musical instruments, such as harmonicas, flutes, clarinets, etc., computer peripherals, communications equipment such as, e.g., telephones, pet accessories such as leashes and carriers, and/or other common household objects could benefit from antimicrobial surfaces.

Materials and procedures have been developed to reduce or prevent a presence of microbes on certain surfaces. For example, compounds which may exhibit antimicrobial activity such as, e.g., certain salts or nanoparticles of silver, can be applied onto or incorporated into certain substrates. Such antimicrobials may be capable of killing or inhibiting growth of certain microbes. Application of such antimicrobial coatings may often be performed using solution chemistry or by combining antimicrobial compounds with polymers, resins, or other materials as part of the casting or manufacturing process whereby those compounds may be incorporated into the final product producing a "treated article". Such materials may often be at least partially organic. However, such coatings may have limited lifetimes for killing or inhibiting growth of microbes. More importantly, such coatings may often not provide a rapid and high level of microbial efficacy which could reduce the risk of microbial contaminants being transferred from one surface to another. Further, such antimicrobial coatings may wear off to some degree when exposed to various environments or conditions (e.g., heat, abrasion, chemicals). Such wear, which can occur rapidly, may reduce or eliminate the ability of these coatings to kill or inhibit growth of microbes over time.

One can see that there is a continuing need for improved antimicrobial cleaners, coatings, and sanitizers which are durable and effective in rapid and high level killing or inhibiting growth of microbes such as bacteria and other microorganisms.

There is a need to provide such materials and coatings which are easy and relatively inexpensive to produce, which have a long life time of killing, which do not wear off easily, and which may be applied to a broad variety of substrates.

In addition, there is a need for such antimicrobial coatings which can be applied to objects that are already in use (clean in place) or that are in need of repair The present invention provides anti-microbial compositions which address one or more of the aforementioned needs as well as others which will become apparent form the description of the invention which follows.

SUMMARY OF THE INVENTION

The anti-microbial compositions of the invention provide a film that is long lasting with residual antimicrobial effect with improved wear resistance when applied to a surface. The compositions comprise a synergistic blend of a quaternary ammonium compound, preferably quaternary ammonium chloride, and cationic biocide such as poly-hexamethylene biguande. In preferred embodiments that compositions also include an amine oxide surfactant (preferably having a carbon chain length of 8), and a chelant (Ethylenediaminetetraacetic acid EDTA) to produce a bacterial/viricidal film that provides both wet efficacy (e.g. when the solution is applied directly to a surface) as well as persistent anti-bacterial/antiviral activity that is significantly more resistant to mechanical abrasion than either of the components alone or in various combinations.

According to the invention the applicants have discovered critical ranges and ratios of the various components that can form a synergistic interaction and improve the anti-microbial coatings of the invention for enhanced wet efficacy, durability and residual anti-microbial activity without causing eye irritation under typical use rates. For example, Applicants have found that a composition of cationic biocide and quaternary ammonium with a ratio of the two components being less than 1:10 (respectively), on an actives weight basis, provides a film forming coating that has residual anti-bacterial activity and improved durability with strong resistance to general wear between applications. In a more preferred embodiment the ratio is about 1:2.5 to about 1:10 and most preferred is a ratio of about 1:2.5 to 1:6.5 of cationic biocide to quaternary ammonium compound (See example #7)

Stated another way, in a use composition, applicants have discovered a critical range of about 1000 to about 6250 ppm quaternary ammonium compound and about 156 (Based on example #9 run @ 0.5 oz/gallon) to 2500 ppm cationic biocide provides a film forming solution that retains its antimicrobial activity and remains on the surface after numerous abrasion cycles. The compositions of the invention comprise at least one quaternary ammonium compounded with the polymeric biguanide.

Applicants surprisingly found that when additional functional components were added to the formulation, residual effectiveness against gram negative organisms was negatively impacted and thus in order to retain enhanced wet efficacy and retain abrasion resistant residual activity, particularly against gram negative organisms, several critical parameters were determined.

For example, Applicants found that as opposed to the larger classes of surfactants, such as alcohol ethoxylates, or sulfonated and sulfated anionic surfactants, instead surfactants used in the compositions are preferably amine oxides and more preferably amine oxides with a carbon chain length of 8. When formulations of the invention were prepared with other surfactants, such as alcohol ethoxylate, the efficacy of the formula was significantly reduced.

Thus Applicants have found that in order to keep efficacy, the ratio of quaternary ammonium to surfactant should be from about 2:1 to about 7:1 respectively on an actives weight basis.

Applicants have also found that the composition preferably includes a chelant. Again here, Applicants have found that the chelant should be in a ratio of from about 2:1 to about 3.5 to 1 of quaternary ammonium to chelant respectively. In a preferred embodiment the chelant is ethylenediaminetetraacetic acid.

In one embodiment the composition of the invention includes a quaternary ammonium compound, a cationic biocide, a chelant, and a surfactant of amine oxide. In a preferred embodiment the invention includes a concentrate composition including from about 1.25% to about 50% wt. % of quaternary ammonium compound, from about 0.125% to about 8.0 wt. % of cationic biocide, from about 0.4% to about 12.8 wt. % of amine oxide, and from about 0.4% to about 12.8% chelant.

In another aspect, the present invention relates to an anti-microbial formulation concentrate that, upon dilution with water, provides a ready to use formulation. In certain embodiments the concentrate composition is diluted with water in a ratio of from about 1:10 to about 1:500, preferably from about 1:30 to about 1:400 and more preferably from about 1:50 to about 1:260 parts of composition to diluent. In a preferred embodiment the above concentrate solution is diluted 1:64.

The invention includes a use solution comprising a use solution of from about 195 ppm to about 7800 ppm of quaternary ammonium compound, from about 19.5 ppm to about 1250 ppm of cationic biocide, from about 62.5 to about 2000 ppm amine oxide, and from about 62.5 to about 2000 ppm chelant.

It is contemplated that formulations comprising the synergistic combination disclosed above can contain additional ingredients as described below and other ingredients that are standard in the art, the compositions of the invention may consist of or consist essentially of the components listed in the paragraph above.

As will be appreciated, the percentage by weight of the components in the compositions of the invention will depend to a large extent on the form in which a composition is provided and the intended use of a composition. It is envisaged that the compositions will be made in a concentrated form and then diluted to a suitable concentration for the intended use. More particularly, it is envisaged that commercially available solutions will include concentrated solutions which can be diluted by the user before use and ready diluted solutions that are ready to use.

The important thing for compositions of the invention to provide the required antimicrobial effect is not typically the concentration of the components in the final solution, rather it is the ratio of the number of molecules of the components. This ratio will remain the same whether the composition is in a concentrated form or whether it is in a dilute (ready-to-use) form.

By the term "anti-microbial" we mean that a compound or composition that kills and/or inhibits the growth of microbes (microorganisms). The term "microbiocidal" is used to refer to compounds or compositions that kill microbes. The compositions of the invention are anti-microbial and/or microbiocidal.

A microorganism or microbe is an organism that is microscopic (too small to be seen by the human eye). Examples of microorganisms include bacteria, fungi, yeasts, moulds, mycobacteria, algae spores, archaea and protists.

Microorganisms are generally single-celled, or unicellular organisms. However, as used herein, the term "microorganisms" also includes viruses.

Preferably, the compositions of the invention comprise at least one cationic anti-microbial agent selected from anti-bacterial, anti-fungal, anti-algal, anti-sporal, anti-viral, anti-yeastal and anti-moldal agents and mixtures thereof. More preferably, the compositions of the invention comprise at least one anti-bacterial, anti-viral, antifungal and/or anti-moldal agent.

As used herein, the terms anti-bacterial, anti-fungal, anti-algal, anti-viral, anti-yeastal and anti-moldal agents are intended to refer to agents, which inhibit the growth of the respective microorganisms but do not necessarily kill the microorganisms and agents which kill the respective microorganisms. Thus, for example, within the term anti-bacterial we include agents, which inhibit the growth of bacteria but may not necessarily kill bacteria and bactericidal agents which do kill bacteria.

As the skilled person will appreciate, the word ending "cidal" as used in for example "bactericidal" and "fungicidal" is used to describe agents which kill the microorganism to which it refers. Thus, in these examples, bactericidal refers to an agent that kills bacteria and fungicidal refers to an agent that kills fungus. Examples of bactericides include myobactericides and tuberculocides. Preferably, the compositions of the invention comprise at least one agent selected from bactericidal, fungicidal, algicidal, sporicidal, virucidal, yeasticidal and moldicidal agents and mixtures thereof. More preferably, the compositions of the invention comprise at least one bactericidal, virucidal, fungicidal and/or moldicidal agent.

"Wet efficacy" is determined by a test process where a liquid suspension of microorganisms is directly combined with a liquid mixture of a chemical disinfectant. The liquid suspension of microorganisms can be added directly to the liquid chemical or chemical can be added directly to the suspension of microorganisms. Alternatively the microorganism suspension may be dried onto a surface thereby creating a "carrier". The carrier can then be added to a liquid mixture of chemistry or the chemistry can be added to the carrier so that in either case microorganisms are combined with a liquid solution of chemistry. Microbial reduction is measured by counting the number of surviving microorganisms following some time period after which disinfectant and microorganisms are combined. That assay is then mathematically converted to a measurement of percent or log reduction of the test organisms.

"Dry efficacy" is determined by a test that measures the antimicrobial effect of a chemical residue dried onto a surface. This takes the form of a chemical being applied to a clean sterilized surface or "carrier". The film is allowed to dry or cure. The carrier is then optionally subjected to simulated "wear" or "abrasion" to test the durability of the surface film. The final step is application of a liquid microorganism suspension to the surface of the dry carrier and assay for survivors following some exposure time. Microbial reduction is measured by counting the number of surviving microorganisms following application of the suspension to the carrier surface. That assay is then mathematically converted to a measurement of percent or log reduction of the test organisms.

The compositions of the invention are effective against a wide range of organisms, including Gram negative and Gram positive spore formers, yeasts, and viruses.

By way of example, the microorganisms which the compositions of the present invention can be effective against include:

Viruses such as HIV-1 (AIDS Virus), Hepatitis B Virus (HVB), Hepatitis C Virus (HCV), Adenovirus, Herpes Simplex, Influenza (including seasonal flu, H1 N1 and H5N1), Respiratory Syncytial Virus (RSV), Vaccinia, Avian Influenza virus, Avian Bronchitis, Pseudorabies virus, Canine Distemper, Newcastle Disease, Rubella, Avian Polyomavirus, Feline leukemia, Feline picornavirus, Infectious Bovine rhinotracheitis, Infectious Bronchitis (Avian IBV)$_1$. Rabies, Transmissible gastroenteritis virus, Marek's Disease.

Funguses such as *Trichophyton mentagrophytes, Aspergillus niger, Candida albicans, Aspergillus flavus, Aspergillus fumigatus, Trichophyton interdigitale, Alternaria tenius, Fusarium oxysporum, Geotrichum candidum, Penicillium digitatum, Phytophthora infestans, Rhizopus nigricans, Trichoderma harzianum, Trichophyton interdigitale.*

Bacteria such as *Pseudomonas aeruginosa, Staphylococcus aureus, Salmonella choleraesuis, Acinetobacter baumannii, Brevibacterium ammoniagenes, Campylobacter jejuni, Enterobacter aerogenes, Escherichia coli, Klebsiella pneumoniae, Proteus mirabilis, Pseudomonas cepacia, Salmonella schottmuelleri, Salmonella typhi, Salmonella typhimurium, Serratia marcescens, Shigella dysenteriae, Shigella flexneri, Shigella sonnei, Staphyloccus epidermidis, Streptoccus faecalis, Streptoccus faecalis* (Vancomycin resistant), *Streptococcus pyogenes, Vibrio chlorae, Xanthomonas axonopodis* pv *citri* (Citrus canker), *Acinetobacter calcoaceticus, Bordetella bronchiseptica, Chlamydia psittaci, Enterobacter cloacae, Enterococcus faecalis, Fusobacterium necrophorum, Legionella pneumophila, Listeria monocytogenes, Pasteurella multocida, Proteus vulgaris, Salmonella enteritidis, Mycoplasma gallisepticum, Yersinia enterocolitica, Aeromonas salmonicida, Pseudomonas putida, Vibrio anguillarum.*

In particular, the compositions of the invention are effective against *P. aeruginosa* (ATCC 15442, PaFH72/a), *E. coli* (ATCC 10536, ECFH64/a, O157:H7 (toxin producing strain), CCFRA/896, O157:H7 (non-toxigenic strain), CCFAA/6896, ATCC 10538), *S. aureus* (including MRSA, (e.g. NCTC 12493 MRSA, ATCC 12493 MRSA), VISA, ATCC 6538, 5a FH73/a), *Entercoccus hirea* (ATCC 10541, EhFH 65/a), Feline Coronavirus (SARS surrogate), Feline Calcivirus (Hum. Norovirus surrogate), *Salmonella typhimurium* (StFH 68/b), *Yersinia enterocolitica* (YE FH67/b), *Listeria monocytogenes* (Lm FH66/c), *Saccharomyces cerevisiae, Bacillus Subtilis* (ATCC 6633), *Bacillus stearothermophilus* (NCTC 10339), *Clostridium dificile* (NCTC 11209), *Candida albicans* (ATCC 1023), *Aspergillus niger* (ATCC 16404), *Mycobacterium smegmatis* (TB stimulant) and Influenza (including seasonal flu, H1 N1 and H5N1).

A further subject-matter of the present invention includes a process for disinfecting and/or cleaning a hard surface. Dilutions for use solutions are preferably within the range of a 1:16 dilution and a 1:256 dilution.

DETAILED DESCRIPTION OF THE INVENTION

Definitions

So that the invention may be more readily understood certain terms are first defined.

"Cleaning" means to perform or aid in soil removal, bleaching, microbial population reduction, or combination thereof.

As used herein, the term "ware" refers to items such as eating and cooking utensils and other hard surfaces such as showers, sinks, toilets, bathtubs, countertops, windows, mirrors, transportation vehicles, and floors. As used herein, the term "warewashing" refers to washing, cleaning, or rinsing ware.

As used herein, the term "hard surface" includes showers, sinks, toilets, bathtubs, countertops, windows, mirrors, transportation vehicles, floors, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of autoclaves and sterilizers, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning using water treated according to the methods of the present invention.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning using water treated according to the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, "weight percent (wt-%)," "percent by weight," "% by weight," and the like are synonyms that refer to the concentration of a substance as the weight of that substance divided by the total weight of the composition and multiplied by 100.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The recitation of numerical ranges by endpoints includes all numbers subsumed within that range (e.g. 1 to 5 includes 1, 1.5, 2, 2.75, 3, 3.80, 4, and 5).

In one aspect, the compositions of the invention must contain critical ratios of a quaternary ammonium compound, and a cationic anti-microbial compound as well as a chelant and surfactant. The anti-microbial agent(s) used in the present invention are preferably water soluble at room temperature and pressure.

Quaternary Ammonium Compounds

Quaternary ammonium compounds, also known as "quats", typically comprise at least one quaternary ammonium cation with an appropriate anion. The quaternary ammonium cations are permanently charged, independent of the pH of their solution. The structure of the cation can be represented as follows:

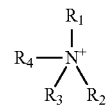

The groups $R_1$, $R_2$, $R_3$ and $R_4$ can vary within wide limits and examples of quaternary ammonium compounds that have anti-microbial properties will be well known to the person of ordinary skill in the art.

Each group $R_1$, $R_2$, $R_3$ and $R_4$ may, for example, independently be a substituted or unsubstituted and/or straight chain or branched and/or interrupted or uninterrupted alkyl, aryl, alkylaryl, arylalkyl, cycloalkyl, (aromatic or non-aromatic) heterocyclyl or alkenyl group. Alternatively, two or more of $R_1$, $R_2$, $R_3$ and $R_4$ may together with the nitrogen atom form a substituted or unsubstituted heterocyclic ring. The total number of carbon atoms in the groups $R_1$, $R_2$, $R_3$ and $R_4$ must be at least 4. Typically the sum of the carbon atoms in the groups $R_1$, $R_2$, $R_3$ and $R_4$ is 10 or more. In a preferred aspect of the invention at least one of the groups $R_1$, $R_2$, $R_3$ and $R_4$ contains from 8 to 18 carbon atoms. For example, 1, 2, 3 or 4 of $R_1$, $R_2$, $R_3$ and $R_4$ can contain from 8 to 18 carbon atoms or 10 to 16 carbon atoms.

Suitable substituents for the groups R-i, $R_2$, $R_3$ and $R_4$ may be selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, —$OR^1$, —$NR^1R''$, —$CF_3$, —CN, —$NO_2$, —$C_2R^1$, —SR', —$N_3$, —C(=O)NR'R'', —$NR^1C(O)$ R'', —C(=O)R\—C(=O)OR\—OC(O)$R^1$, —O(CR'R$^x$)$_r$C(=O)R', O (CR'R'')$_r$NR''C(O)R', —O(CR'R'')$_r$NR''SO$_2$R', —OC(O)$NR^1R''$, —$NR^1$C(O)OR'', —SO$_2$R', —SO$_2$$NR^1R''$, and —$NR^1SO_2R''$, wherein $R^1$ and R'' are individually hydrogen, $C_1$-$C_8$ alkyl, cycloalkyl, heterocyclyl, aryl, or arylalkyl, and r is an integer from 1 to 6, or R' and R'' together form a cyclic functionality, wherein the term "substituted" as applied to alkyl, alkenyl, heterocyclyl, cycloalkyl, aryl, alkylaryl and arylalkyl refers to the substituents described above, starting with F and ending with —NR$^1$SO$_2$R".

When one or more of R$_1$, R$_2$, R$_3$ and R$_4$ is interrupted, suitable interrupting groups include but are not limited to heteroatoms such as oxygen, nitrogen, sulphur, and phosphorus-containing moieties (e.g. phosphinate). A preferred interrupting group is oxygen.

Suitable anions for the quats include but are not limited to halide anions such as chloride, fluoride, bromide or iodide and the non-halide sulphonate.

Preferred quats are those having the formula: $(CH_3)_n(A)_m N^+X$— wherein A may be as defined above in relation to R$_1$, R$_2$, R$_3$ and R$_4$. X" is selected from chloride, fluoride, bromide or iodide and sulphonate (preferably chloride or bromide), n is from 1 to 3 (preferably 2 or 3) and m is from 1 to 3 (preferably 1 or 2) provided that the sum of n and m is 4. Preferably, A is a C$_{6-20}$ (e.g. C$_{8-18}$, i.e. having 8, 9, 10, 11, 12, 13, 14, 15, 16, 17 or 18 carbon atoms or C$_{8-12}$ or C$_{12-18}$) substituted or unsubstituted and/or straight chain or branched and/or interrupted or uninterrupted alkyl, aryl, alkylaryl, arylalkyl or cycloalkyl group (wherein suitable substituents are as defined above in relation to R$_1$, R$_2$, R$_3$ and R$_4$). Each group A may be the same or different.

A preferred group of the compounds of formula $(CH_3)_n (A)_m N^+X'$ are those wherein n=3 and m=1. In such compounds A may be as defined above and is preferably a C$_{6-20}$ substituted or unsubstituted and/or straight chain or branched and/or interrupted or uninterrupted alkyl, aryl, or alkylaryl group. Examples of this type of quaternary ammonium compound include Cetrimide (which is predominately trimethyltetradecylammonium bromide), dodecyltrimethyl-ammonium bromide, trimethyltetradecylammonium bromide, hexadecyltrimethylammonium bromide.

Another preferred group of the compounds of formula $(CH_3)_n(A)_m N^+X'$ are those wherein n=2 and m=2. In such compounds A may be as defined above in relation to R$_1$, R$_2$, R$_3$ and R$_4$. Preferably A is a C$_{6-20}$ substituted or unsubstituted and/or straight chain or branched and/or interrupted or uninterrupted alkyl, aryl, or alkylaryl group. For example, A may represent a straight chain, unsubstituted and uninterrupted C$_{8-12}$ alkyl group or a benzyl group. In these compounds, the groups A may be the same or different. Examples of this type of compound include didecyl dimethyl ammonium chloride and dioctyl dimethyl ammonium chloride.

Examples of the preferred quaternary ammonium compounds described above include the group of compounds which are generally called benzalkonium halides and aryl ring substituted derivatives thereof. Examples of compounds of this type include benzalkonium chloride, which has the structural formula:

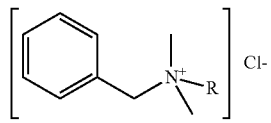

wherein R may be as defined above in relation to R$_1$, R$_2$, R$_3$ and R$_4$. Preferably, R is a C$_{8-18}$ alkyl group or the benzalkonium chloride is provided and/or used as a mixture of C$_{8-18}$ alkyl groups, particularly a mixture of straight chain, unsubstituted and uninterrupted alkyl groups n-C$_8$H17 to n-C$_{18}$H$_{37}$, e.g. n-Ci$_2$H$_{25}$ to n C$_{18}$H$_{37}$ mainly n-C$_{12}$H$_{25}$ (dodecyl), n-C$_{14}$H$_{29}$ (tetradecyl), and n-C$_{16}$H$_{33}$ (hexadecyl).

Other preferred quaternary ammonium compounds include those in which the benzene ring is substituted, for example alkyldimethyl ethylbenzyl ammonium chloride. As an example, a mixture containing, for example, equal molar amounts of alkyl dimethyl benzyl ammonium chloride and alkyldimethyl ethylbenzyl ammonium chloride may be used.

Other quaternary ammonium compounds suitable for use in the invention include, but are not limited to, alkylpyridinium compounds, such as cetylpyridinium chloride, and bridged cyclic amino compounds such as the hexaminium compounds.

Other examples of quats which may be used in the present invention include Cetalkonium Chloride, Cetylpyridinium Chloride, Glycidyl Trimethyl Ammonium Chloride, Stearalkonium Chloride; Zephiran chloride (R); Hyamine 3500; Diisobutylphenoxyethoxyethyldimethylbenzylammonium chloride; Hyamine 1622(R); Cetalkonium Chloride; Cetyldimethylbenzyl-ammonium chloride; Triton K 12; Cetyltrimethylammonium bromide; Retarder LA; 1-Hexadecylpyridinium chloride; Glycidyltrimethyl-ammonium chloride; Benzethonium Chloride CAS 121-54-0; Cetalkonium Chloride CAS 122-18-9; Cetrimide CAS 8044-71-1; Cetylpyridinium Chloride (anhydrous) CAS 123-03-5; Stearalkonium Chloride CAS 122-19-0; Cetrimonium Bromide CAS 57-09-0.

Particularly preferred quaternary ammonium compounds include benzyldimethyl-n-tetradecyl-ammonium chloride, benzyldimethyl-n-dodecyl-ammonium chloride, n-dodecyl-n-tetradecyldimethyl-ammonium chloride and benzyl-Ci$_2$-C$_{16}$-alkyl-dimethyl-ammonium chloride, benzyl-cocoalkyl-dimethyl-ammonium chloride, di-n-decyldimethylammonium chloride.

The compositions of the invention include a synergistic combination of a cationic anti-microbial, a chelant and an amine oxide surfactant in combination with the quaternary ammonium compound.

According to the invention the applicants have discovered that a use solution composition in the critical range of about 195 to about 7800 ppm of a single quaternary ammonium compound, about 19.5 to about 1250 ppm of cationic biocide provides a film forming solution that retains its antimicrobial activity and remains on the surface after numerous abrasion cycles. In additional preferred embodiments the use composition also includes from about 62.5-2000 ppm amine oxide surfactant and 62.5 to 2000 ppm chelant.

On an actives weight basis, the invention comprises a ratio of cationic biocide to single quaternary ammonium compound to of about 1:10 to about 1:0.5 More preferred is a range of about 1:6.0 to about 1:1.0 and most preferred is a ratio of about 1:4.0 to about 1:2.0.

In a preferred embodiment the ratio of cationic biocide to one or more quaternary ammonium is less than 1:1 (i.e. less than 50% by weight of cationic biocide. In a more preferred embodiment the ratio is from about 0.99 to about 0.01 cationic biocide to about 1 of quaternary ammonium on an actives weight basis. These compositions of the invention comprise at least one cationic biocide, but they preferably do not contain more than a single class of quaternary ammonium compound Thus Applicants have found that in order to keep efficacy, the ratio of quaternary ammonium to surfactant should be from about 2:1 to about 7:1 respectively.

Applicants have also found that the composition preferably includes a chelant. Again here, Applicants have found that the chelant should be in a ration of from about 2:1 to about 3.5 to 1 of quaternary ammonium to chelant respectively. In a preferred embodiment the chelant is ethylenediaminetetraacetic acid.

Cationic Biocide

The cationic biocide agent is that component of the composition provides at least part of the biocidal/antimicrobial activity. That is, the cationic biocide agent has at least some biocidal/antimicrobial activity for at least one microorganism. It is generally considered the main active component of the compositions described herein. The cationic biocide agent includes an effective amount of one or more biocide agents selected from the group consisting of biguanides and bisbiguanides such as chlorhexidine and its various salts including but not limited to the digluconate, diacetate, dimethosulfate, and dilactate salts, as well as combinations thereof; polymeric quaternary ammonium compounds such as polyhexamethylenebiguanide; small molecule quaternary ammonium compounds such as benzalkonium halides; and compatible combinations thereof. It is particularly important, however, with cationic biocide agents in a salt form to use a counter ion that ensures solubility in aqueous fluid above the minimum inhibitory concentration (MIC) of the treatment organism. If the solubility limit is less than the MIC, treatment may be ineffective.

The classes of cationic biocide agent suitable in the present invention are discussed further below.

Biguanides

This class of biocides is represented by the formula:

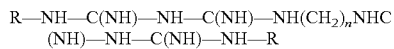
R—NH—C(NH)—NH—C(NH)—NH(CH$_2$)$_n$NHC(NH)—NH—C(NH)—NH—R

Where n=3-10, preferably 4-8, and most preferably 6; and R is C$_4$-C$_1$ branched or straight chain alkyl optionally substituted in available positions by halogen or C$_6$-C$_{12}$ aryl or alkaryl optionally substituted in available positions by halogen.

The preferred compound of this class is chlorhexidine. This may be present as the free base but is preferably present as a disalt of acetate, gluconate, lactate, methosulfate (CH$_3$OSO$_3^-$), or a halide or combinations thereof. The most preferred compound is chlorhexidine digluconate (CHG). Other anions may be useful. Many salts of chlorhexidine have high solubility (>1 g/100 mL) in alcohol/water systems and are therefore useful in compositions of this invention.

The biocides of this class are particularly preferred in formulations that are aqueous and protected from light. This is believed to reduce the degradation of the compound. Care must also be taken when formulating chlorhexidine as well as other cationic biocide compounds to avoid inactivation by sequestering it in micelles which may be formed by incorporation of surfactants and/or emulsifiers. Preferred compositions of this invention are essentially free of surfactants and/or emulsifiers.

Bis(biguanide)s such as chlorhexidine are very basic and capable of forming multiple ionic bonds with anionic materials. For this reason, biguanide-containing compositions are preferably free of anionic compounds that can result in precipitation of the biocide. Anionic surfactants useful, for example, as wetting agents, may also need to be avoided. Halide salts may need to be avoided. For example, chlorhexidine digluconate (CHG) will precipitate rapidly in the presence of halide salts above a concentration of about 0.1M. Therefore, if a system includes CHG or other biocide of this class, and needs to comprise salts for stability or other purposes, preferably gluconate salts such as triethanolamine gluconate or sodium gluconate, are used.

It has been found that in use compositions of the invention which comprise the two components of a quaternary ammonium compound and a cationic biocide in for example the ratios set out above have an advantageous anti-microbial effect. For example, such compositions can have an enhanced kill rate when they are applied to a surface (so called "wet kill") and/or they can also have a residual anti-microbial effect in that they control, reduce or prevent the formation of new microbial colonies at the surface (so called "dry kill") and/or they are effective at significantly lower concentration of anti-microbial agent than previously known compositions.

Surfactants

In some embodiments, the compositions of the present invention include a surfactant. Surfactants suitable for use with the compositions of the present invention include, but are not limited to, semi-polar nonionic surfactants such as amine oxides. In addition, other surfactants such as anionic surfactants, and zwitterionic surfactants may be used. In some embodiments, the compositions of the present invention include about 0.4 wt % to about 12.8 wt % of a surfactant. In some embodiments, the compositions of the present invention include about 62.5 ppm to about 2000 ppm of a surfactant.

Semi-Polar Nonionic Surfactants

The semi-polar type of nonionic surface active agents are the preferred class of surfactants useful in compositions of the present invention. Semi-polar nonionic surfactants include the amine oxides, phosphine oxides, sulfoxides and their alkoxylated derivatives. Most preferred are amine oxide surfactants of am R$^1$ chain length of 8.

Amine oxides are tertiary amine oxides corresponding to the general formula:

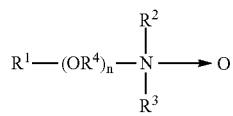

$$R^1-(OR^4)_n-\underset{R^3}{\overset{R^2}{N}}\longrightarrow O$$

wherein the arrow is a conventional representation of a semi-polar bond; and, R$^1$, R$^2$, and R$^3$ may be aliphatic, aromatic, heterocyclic, alicyclic, or combinations thereof. Generally, for amine oxides of detergent interest, R$^1$ is an alkyl radical of from about 8 to about 24 carbon atoms; R$^2$ and R$^3$ are alkyl or hydroxyalkyl of 1-3 carbon atoms or a mixture thereof; R$^2$ and R$^3$ can be attached to each other, e.g. through an oxygen or nitrogen atom, to form a ring structure; R$^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

The compositions of the invention may optionally include additional surfactants such as the following.

Nonionic Surfactants

Suitable additional nonionic surfactants for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC11; mixtures thereof, or the like.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

R—O—$(CH_2CH_2O)_n(CH_2)_m$—$CO_2X$ (3)

in which R is a $C_8$ to $C_{22}$ alkyl group or

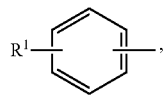

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_5$-$C_{16}$ alkyl group. In some embodiments, R is a $C_{12}$-$C_{14}$ alkyl group, n is 4, and m is 1.

In other embodiments, R is

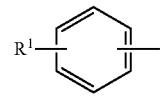

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

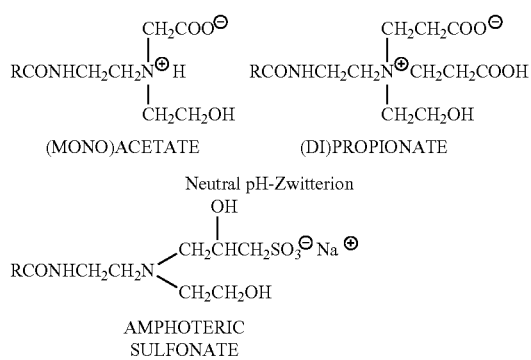

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+$($CH_2$—$CH_2$—$CO_2Na)_2$—$CH_2$—$CH_2$—OH or $C_{12}$-alkyl-C(O)—N(H)—$CH_2$—$CH_2$—$N^+(CH_2$—$CO_2Na)_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

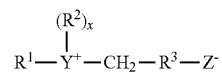

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

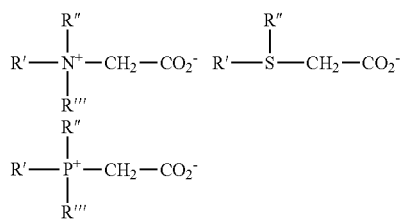

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2 \, N^+ \, R^2SO^{3-}$, in which R is a $C_6$-$C_{18}$ hydrocarbyl group, each $R^1$ is typically independently $C_1$-$C_3$ alkyl, e.g. methyl, and $R_2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Chelants

The compositions of the invention can also include a chelant at a level of from 0.4 wt. % to 12.8 wt. %, or 62.5 ppm to about 2000 ppm in a use composition. Chelation herein means the binding or complexation of a bi- or multidentate ligand. These ligands, which are often organic compounds, are called chelants, chelators, chelating agents, and/or sequestering agent. Chelating agents form multiple bonds with a single metal ion. Chelants, are chemicals that form soluble, complex molecules with certain metal ions, inactivating the ions so that they cannot normally react with other elements or ions to produce precipitates. The ligand forms a chelate complex with the substrate. The term is reserved for complexes in which the metal ion is bound to two or more atoms of the chelant.

Suitable chelating agents can be selected from the group consisting of amino carboxylates, amino phosphonates, polyfunctionally-substituted aromatic chelating agents and mixtures thereof. Preferred chelants for use herein are amino carboxylates.

Amino carboxylates include ethylenediaminetetra-acetates, N-hydroxyethylethylenediaminetriacetates, nitrilotriacetates, ethylenediamine tetrapro-prionates, triethylenetetraaminehexacetates, diethylenetriaminepentaacetates, and ethanoldi-glycines, alkali metal, ammonium, and substituted ammonium salts therein and mixtures therein. As well as MGDA (methyl-glycine-diacetic acid), and salts and derivatives thereof and GLDA (glutamic-N,N-diacetic acid) and salts and derivatives thereof. GLDA (salts and derivatives thereof) is especially preferred according to the invention, with the tetrasodium salt thereof being especially preferred.

Other suitable chelants include amino acid based compound or a succinate based compound. The term "succinate based compound" and "succinic acid based compound" are used interchangeably herein. Other suitable chelants are described in U.S. Pat. No. 6,426,229. Particular suitable chelants include; for example, aspartic acid-N-monoacetic acid (ASMA), aspartic acid-N,N-diacetic acid (ASDA), aspartic acid-N-monopropionic acid (ASMP), iminodisuccinic acid (IDS), Imino diacetic acid (IDA), N-(2-sulfomethyl)aspartic acid (SMAS), N-(2-sulfoethyl)aspartic acid (SEAS), N-(2-sulfomethyl)glutamic acid (SMGL), N-(2-sulfoethyl)glutamic acid (SEGL), N-methyliminodiacetic acid (MIDA), .quadrature.-alanine-N,N-diacetic acid (.quadrature.-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts or ammonium salts thereof. Also suitable is ethylenediamine disuccinate ("EDDS"), especially the [S,S] isomer as described in U.S. Pat. No. 4,704,233. Furthermore, Hydroxyethyleneiminodiacetic acid, Hydroxyiminodisuccinic acid, Hydroxyethylene diaminetriacetic acid is also suitable.

Other chelants include homopolymers and copolymers of polycarboxylic acids and their partially or completely neutralized salts, monomeric polycarboxylic acids and hydroxycarboxylic acids and their salts. Preferred salts of the abovementioned compounds are the ammonium and/or alkali metal salts, i.e. the lithium, sodium, and potassium salts, and particularly preferred salts are the sodium salts.

Suitable polycarboxylic acids are acyclic, alicyclic, heterocyclic and aromatic carboxylic acids, in which case they contain at least two carboxyl groups which are in each case separated from one another by, preferably, no more than two carbon atoms. Polycarboxylates which comprise two carboxyl groups include, for example, water-soluble salts of, malonic acid, (ethyl enedioxy) diacetic acid, maleic acid, diglycolic acid, tartaric acid, tartronic acid and fumaric acid. Polycarboxylates which contain three carboxyl groups include, for example, water-soluble citrate. Correspondingly, a suitable hydroxycarboxylic acid is, for example, citric acid. Another suitable polycarboxylic acid is the homopolymer of acrylic acid. Preferred are the polycarboxylates end capped with sulfonates.

Amino phosphonates are also suitable for use as chelating agents and include ethylenediaminetetrakis(methylenephosphonates) as DEQUEST. Preferred, these amino phosphonates that do not contain alkyl or alkenyl groups with more than about 6 carbon atoms.

Polyfunctionally-substituted aromatic chelating agents are also useful in the compositions herein such as described in U.S. Pat. No. 3,812,044. Preferred compounds of this type in acid form are dihydroxydisulfobenzenes such as 1,2-dihydroxy-3,5-disulfobenzene.

Further suitable polycarboxylates chelants for use herein include citric acid, lactic acid, acetic acid, succinic acid, formic acid all preferably in the form of a water-soluble salt. Other suitable polycarboxylates are oxodisuccinates, carboxymethyloxysuccinate and mixtures of tartrate monosuccinic and tartrate disuccinic acid such as described in U.S. Pat. No. 4,663,071.

Other Additional Ingredients

Additional ingredients that may be used in the formulations of the invention include but are not limited to water, antioxidants, thickeners, foam makers/boosters such as alkanolamides and abrasives, sequestrants such as nitrilotriacetic acid (NTA), tetrasodium EDTA, other acetic acid derivatives and mixtures thereof, salts such as sodium chloride and citrate salts, pH modifiers, for example acids such as citric, sulfamic, hydrochloric, phosphoric, nitric, lactic, formic, acetic or gluconic acids or other mineral or organic acids or bases such as sodium or potassium hydroxide and mono-, di- or tri-ethanoiamine, colorants, fragrances, emollients and hair and/or skin rejuvenating and/or protecting agents.

In some embodiments, the compositions of the present invention can include other additional ingredients. Additional ingredients suitable for use with the compositions of the present invention include, but are not limited to, acidulants, stabilizing agents, buffers, detergents, wetting agents, defoaming agents, thickeners, aesthetic enhancing agents (i.e., colorants, odorants, or perfumes) and other cleaning agents. These additional ingredients can be preformulated with the compositions of the invention or added to the system before, after, or substantially simultaneously with the addition of the compositions of the present invention. Additionally, the compositions can be used in conjunction with one or more conventional cleaning agents.

Acidulants

In some embodiments, the compositions of the present invention include an acidulant. The acidulant can act as a catalyst for conversion of carboxylic acid to peroxycarboxylic acid. The acidulant can be effective to form a concentrate composition with pH of about 1 or less. The acidulant can be effective to form a use composition with pH of about 5, about 5 or less, about 4, about 4 or less, about 3, about 3 or less, about 2, about 2 or less, or the like. In some embodiments, an acidulant can be used to lower the pH of an alkaline cleaning solution to a pH of about 10, about 10 or less, about 9, about 9 or less, about 8, about 8 or less, about 7, about 7 or less, about 6, or about 6 or less. In an embodiment, the acidulant includes an inorganic acid. Suitable inorganic acids include, but are not limited to, sulfuric acid, sodium bisulfate, phosphoric acid, nitric acid, hydrochloric acid. In some embodiments, the acidulant includes an organic acid. Suitable organic acids include, but are not limited to, methane sulfonic acid, ethane sulfonic acid, propane sulfonic acid, butane sulfonic acid, xylene sulfonic acid, benzene sulfonic acid, formic acid, acetic acid, mono, di, or tri-halocarboyxlic acids, picolinic acid, dipicolinic acid, and mixtures thereof. In some embodiments, the compositions of the present invention are free or substantially free of a phosphorous based acid.

In some embodiments, acidulant selected can also function as a stabilizing agent. Thus, the compositions of the present invention can be substantially free of an additional stabilizing agent.

Stabilizing Agents In some embodiments, the compositions of the present invention include one or more stabilizing agents in addition to the chelant component mentioned supra. The stabilizing agents can be used, for example, to stabilize the composition components and prevent their interaction.

Suitable stabilizing agents include, for example, chelating agents or sequestrants. Suitable sequestrants include, but are not limited to, organic chelating compounds that sequester metal ions in solution, particularly transition metal ions. Such sequestrants include organic amino- or hydroxy-poly-phosphonic acid complexing agents (either in acid or soluble salt forms), carboxylic acids (e.g., polymeric polycarboxylate), hydroxycarboxylic acids, aminocarboxylic acids, or heterocyclic carboxylic acids, e.g., pyridine-2,6-dicarboxylic acid (dipicolinic acid).

In some embodiments, the compositions of the present invention include dipicolinic acid as a stabilizing agent. Compositions including dipicolinic acid can be formulated to be free or substantially free of phosphorous. It has also been observed that the inclusion of dipicolinic acid in a composition of the present invention aids in achieving the phase stability of the compositions, compared to other conventional stabilizing agents, e.g., 1-hydroxy ethylidene-1,1-diphosphonic acid ($CH_3C(PO_3H_2)_2OH$) (HEDP).

In other embodiments, the sequestrant can be or include phosphonic acid or phosphonate salt. Suitable phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are included in the compositions of the present invention.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), ($N[CH_2PO_3H_2]_3$), available from Monsanto as DEQUEST® 2000; ethylenediamine[tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N,N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed poly acrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

Wetting or Defoaming Agents

Also useful in the compositions of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfonated or sulfated derivatives; fatty acids and/or their soaps such as alkali, alkaline earth metal soaps; and phosphates and phosphate esters such as alkyl and alkaline diphosphates, and tributyl phosphates among others; and mixtures thereof.

In some embodiments, the compositions of the present invention can include antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others.

Thickening or Gelling Agents

The compositions of the present invention can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition.

Solidification Agent

The present compositions can include a solidification agent, which can participate in maintaining the compositions in a solid form. In some embodiments, the solidification agent can form and/or maintain the composition as a solid. In other embodiments, the solidification agent can solidify the composition without unacceptably detracting from the eventual release of the sulfonated peroxycarboxylic acid. The solidification agent can include, for example, an organic or inorganic solid compound having a neutral inert character or making a functional, stabilizing or detersive contribution to the present composition. Suitable solidification agents include solid polyethylene glycol (PEG), solid polypropylene glycol, solid EO/PO block copolymer, amide, urea (also known as carbamide), nonionic surfactant (which can be employed with a coupler), anionic surfactant, starch that has been made water-soluble (e.g., through an acid or alkaline treatment process), cellulose that has been made water-soluble, inorganic agent, poly(maleic anhydride/methyl vinyl ether), polymethacrylic acid, other generally functional or inert materials with high melting points, mixtures thereof, and the like;

Suitable glycol solidification agents include a solid polyethylene glycol or a solid polypropylene glycol, which can, for example, have molecular weight of about 1,400 to about 30,000. In certain embodiments, the solidification agent includes or is solid PEG, for example PEG 1500 up to PEG 20,000. In certain embodiments, the PEG includes PEG 1450, PEG 3350, PEG 4500, PEG 8000, PEG 20,000, and the like. Suitable solid polyethylene glycols are commercially available from Union Carbide under the tradename CARBOWAX.

Suitable amide solidification agents include stearic monoethanolamide, lauric diethanolamide, stearic diethanolamide, stearic monoethanol amide, cocodiethylene amide, an alkylamide, mixtures thereof, and the like. In an embodiment, the present composition can include glycol (e.g., PEG) and amide.

Suitable nonionic surfactant solidification agents include nonylphenol ethoxylate, linear alkyl alcohol ethoxylate, ethylene oxide/propylene oxide block copolymer, mixtures thereof, or the like. Suitable ethylene oxide/propylene oxide block copolymers include those sold under the Pluronic tradename (e.g., Pluronic 108 and Pluronic F68) and commercially available from BASF Corporation. In some embodiments, the nonionic surfactant can be selected to be solid at room temperature or the temperature at which the composition will be stored or used. In other embodiments, the nonionic surfactant can be selected to have reduced aqueous solubility in combination with the coupling agent. Suitable couplers that can be employed with the nonionic surfactant solidification agent include propylene glycol, polyethylene glycol, mixtures thereof, or the like.

Suitable anionic surfactant solidification agents include linear alkyl benzene sulfonate, alcohol sulfate, alcohol ether sulfate, alpha olefin sulfonate, mixtures thereof, and the like. In an embodiment, the anionic surfactant solidification agent is or includes linear alkyl benzene sulfonate. In an embodiment, the anionic surfactant can be selected to be solid at room temperature or the temperature at which the composition will be stored or used.

Suitable inorganic solidification agents include phosphate salt (e.g., alkali metal phosphate), sulfate salt (e.g., magnesium sulfate, sodium sulfate or sodium bisulfate), acetate salt (e.g., anhydrous sodium acetate), Borates (e.g., sodium borate), Silicates (e.g., the precipitated or fumed forms (e.g., Sipernat 50® available from Degussa), carbonate salt (e.g., calcium carbonate or carbonate hydrate), other known hydratable compounds, mixtures thereof, and the like. In an embodiment, the inorganic solidification agent can include organic phosphonate compound and carbonate salt, such as an E-Form composition.

In some embodiments, the compositions of the present invention can include any agent or combination of agents that provide a requisite degree of solidification and aqueous solubility can be included in the present compositions. In other embodiments, increasing the concentration of the solidification agent in the present composition can tend to increase the hardness of the composition. In yet other embodiments, decreasing the concentration of solidification agent can tend to loosen or soften the concentrate composition.

In some embodiments, the solidification agent can include any organic or inorganic compound that imparts a solid character to and/or controls the soluble character of the present composition, for example, when placed in an aqueous environment. For example, a solidifying agent can provide controlled dispensing if it has greater aqueous solubility compared to other ingredients in the composition.

Urea can be one such solidification agent. By way of further example, for systems that can benefit from less aqueous solubility or a slower rate of dissolution, an organic nonionic or amide hardening agent may be appropriate.

In some embodiments, the compositions of the present invention can include a solidification agent that provides for convenient processing or manufacture of the present composition. For example, the solidification agent can be selected to form a composition that can harden to a solid form under ambient temperatures of about 30 to about 50° C. after mixing ceases and the mixture is dispensed from the mixing system, within about 1 minute to about 3 hours, or about 2 minutes to about 2 hours, or about 5 minutes to about 1 hour.

The compositions of the present invention can include solidification agent at any effective amount. The amount of solidification agent included in the present composition can vary according to the type of composition, the ingredients of the composition, the intended use of the composition, the quantity of dispensing solution applied to the solid composition over time during use, the temperature of the dispensing solution, the hardness of the dispensing solution, the physical size of the solid composition, the concentration of the other ingredients, the concentration of the cleaning agent in the composition, and other like factors. Suitable amounts can include about 1 to about 99 wt-%, about 1.5 to about 85 wt-%, about 2 to about 80 wt-%, about 10 to about 45 wt-%, about 15% to about 40 wt-%, about 20% to about 30 wt-%, about 30% to about 70%, about 40% to about 60%, up to about 50 wt-%, about 40% to about 50%

Use Compositions

The compositions of the present invention include concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired activity of the antimicrobial composition. Generally, a dilution of about 1 fluid ounce to about 10 gallons of water to about 10 fluid ounces to about 1 gallon of water is used for aqueous compositions of the present invention. In some embodiments, higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 40 ounces of concentrate per 100 gallons of water.

In certain embodiments, a use composition can include about 0.01 to about 10 wt-% of a concentrate composition and about 90 to about 99.99 wt-% diluent; or about 0.1 to about 1 wt-% of a concentrate composition and about 99 to about 99.9 wt-% diluent.

Amounts of an ingredient in a use composition can be calculated from the amounts listed herein for concentrate compositions and these dilution factors. The concentrated compositions of the present invention are generally diluted such that the quaternary ammonium compound is present at from about 195 ppm to about 7800 ppm and the cationic biocide is present from about 19.5 to 1250. It is to be understood that all values and ranges between these values and ranges are encompassed by the present invention.

The compositions of the invention are resistant to touching and general abrasion. This means that the compositions of the invention provide a residual anti-microbial effect even when the surface is touched, rubbed or abraded as would be typical during normal interaction between a surface and individuals working on or around that surface. The durability of the antimicrobial film is not intended to be permanent but it can be replenished by wiping the treated surface with a saturated cloth, mop, sponge or other suitable delivery mechanism. The composition can also be applied by spraying or flooding the surface with the biocidal composition. The synergistic combination of the components increases durability of the film, making it more resistant to wear and abrasion.

It will be appreciated that the actual concentration of components in a composition of the invention will depend on the intended use of that composition. For disinfecting uses, such as cleaning of hospital wards and equipment to help prevent the spread of disease such as MRSA, higher concentrations are required than for certain sanitizing applications.

In use the compositions of the invention act to substantially reduce or control the formation of microbial colonies on or at the surface to which they are applied. This means that not only do the compositions of the invention kill any microorganisms that are present on a surface when they are applied to that surface (so called "wet kill"), they also have a residual effect in that they prevent the formation of new microbial colonies at the surface (so called "dry kill").

The present compositions provide improved durability, i.e. the compositions of the invention remain on the surface and prevent the growth of colonies of microorganisms. The residual effect can often be seen even after a treated surface has been touched or abraded numerous times.

Anti-microbial compositions are considered to have residual efficacy if, in the residual efficacy test described herein, they give a reduction in the number of microorganisms which is at least log 3.0. Preferably an anti-microbial composition having a residual effect and tested in this manner will give a log reduction of at least about 3.0, more preferably at least about 4.0 and most preferably about 6.0 or more, up to total kill or substantially total kill (zero survivors) under the test conditions described above.

In a particular aspect, the present invention provides anti-microbial compositions which have residual efficacy. In other words these compositions, when tested in accordance with the residual efficacy test described herein have an anti-microbial efficacy within the parameter set out in the paragraph above.

The formulations of the present invention typically comprise an anti-microbial composition as described above in combination with compatible ingredients which allow the formulation to perform its primary purpose.

In particular, the present invention provides formulations comprising an antimicrobial compositions suitable for a variety of consumer applications. Examples of the formulations of the invention include, but are not limited to, surface cleaners such as those intended for use in bathrooms, kitchens, living areas, hard floor cleaners, carpet cleaners, furniture cleaners, glass/mirror cleaners; toilet care products including solid toilet cleaners such as rim devices and those designed to be placed in the cistern, liquid toilet cleaners excluding those comprising hypochlorite bleaches; dishwashing products such as washing up liquids and preparations from dishwashing machines such as dishwashing solids (e.g. powders and tablets) & liquids; laundry products such as solid detergents (e.g. powders and tablets), liquid detergents and fabric conditioners and "2 in 1" products comprising detergent and fabric conditioner; cleaning products intended for use outdoors such as those for cleaning for wood, stone, concrete or plastics, for example patio cleaner, garden furniture cleaners/treatments, BBQ cleaners, wall and fence cleaners/treatments, plant sprays such as those intended to remove insects such as aphides from plants; food sprays, such as those suitable for use in food preservation; personal care products such as bath and shower products; soaps, including liquid and solid soaps, hand sanitizers, deodorants and antiperspirants, hair care products including shampoos, for example anti-scalp odor shampoos, shampoos for the control of head lice eggs and anti-dandruff shampoos, hair conditioners, hair styling products such as hair mousses, gels and sprays, skin care products such as shaving products, cosmetics and products for hair removal; baby products including baby cleaning and cleansing products such as baby bath, soaps, wipes, moisturizers, nappy rash cream, products for cleaning surfaces that have regular & high incidence of infant & baby contact; first aid products and products for treating ailments and illnesses, including products for the topical treatment and/or prevention of minor infections such as athletes foot, spot/acne prevention/treatment products; foot hygiene products, including those for use on the foot and those for the treatment/deodorization of foot ware, particularly sports foot wear; products for cleaning and/or deodorizing vehicles such as cars.

The formulations of the invention comprise an anti-microbial composition as described above. The pH of the formulations of the invention can vary within wide limits. Typically, the pH of a formulation of the invention will be similar to that of known formulations which are intended to be used for the same purpose or a similar purpose to a given formulation of the invention. For example The pH can range from 4 to 11 depending on the dilution, and specific use of the composition.

Examples of formulations of the invention are as follows:
Below is a use composition of the invention.

|  | Preferred | More Preferred | Most preferred |
| --- | --- | --- | --- |
| Quaternary ammonium | 195-7800 ppm | 390-3906 ppm | 780-1953 ppm |
| Cationic biocide | 19.5-1250 ppm | 87.5-937.5 ppm | 156-625 ppm |
| Amine Oxide | 62.5-2000 ppm | 125-1500 ppm | 250-1000 ppm |
| Chelant | 62.5-2000 ppm | 125-1500 ppm | 250-1000 ppm |

The following is a concentrate composition that can be diluted at a 1:64 ratio.

|  | Preferred | More Preferred | Most preferred |
| --- | --- | --- | --- |
| Quaternary ammonium | 1.25-50% | 2.5-25% | 5-12.5% |
| Cationic | 0.125-8.0% | 0.56-6.0% | 1.0-4% |
| Amine Oxide | 0.4-12.8% | 0.8-9.6% | 1.6-6.4% |
| Chelant | 0.4-12.8% | 0.8-9.6% | 1.6-6.4% |

Typically, the anti-microbial composition is incorporated into a simple conventional detergent solution or added to a "final rinse" during cleaning.

According to a further aspect of the invention, there is provided the use of an antimicrobial composition of the invention to prevent the formation of colonies of microorganisms on a surface at which it is provided.

According to yet a further aspect of the invention, there is provided the use of a formulation to prevent the formation of colonies of microorganisms on a surface at which it is provided.

The invention also provides a process for making the compositions of the invention. The process comprises the steps of (A) mixing at least part of quaternary ammonium compound and adding the cationic biocide component in the appropriate amounts to achieve the synergy of the two, and any further components such as chelants, and surfactants, and agitating the resulting mixture until a clear solution is formed.

Typically, the process to produce the compositions of the invention is carried out at room temperature with stirring.

The present invention provides compositions obtainable by the process set out above. The compositions of the invention may be prepared in a concentrated form (i.e. with little or no polar solvent) and diluted with water when used.

The following are non-limiting examples of the invention and are intended for purposes of illustration only.

EXAMPLES

Example 1

Hard Surface Efficacy of PHMB/Quaternary Ammonium Chloride Blend Vs. Stabilized Chlorine Dioxide The objective of this analysis was to examine the efficacy of various compositions against *Staphylococcus aureus* ATCC 6538 and *Klebsiella pneumoniae* ATCC 4352 after application to inanimate, non-porous, non-food contact surfaces.

Test Method:
Residual Self-Sanitizing Activity on Hard, Non-Porous Surfaces
  Test Surface Preparation:
    Clean glass test surfaces were decontaminated by immersing in reagent alcohol and allowing to air dry at room temperature. The test surfaces were dried in sterile glass petri dishes containing 2 layers of Whatman No. 2 paper. Each petri dish had two surfaces in them and were dried for 1 day in a biological safety cabinet with the lids cracked open.
  Test Surface Inoculation and Coating:
    The initial inoculum suspension was prepared by making $10^{-2}$ and $10^{-4}$ dilutions from a 48-54 hour broth culture of the test system. The $10^{-4}$ dilution was allowed to stand for 15 minutes before 10 µL was spread evenly over the entire coupon. The coupons were dried at 35±2° C. for 30 minutes with the lids cracked open. 50 µL of the diluted test substances of 0.01% Triton X 100 (for controls) was gently spread over the surface of the coupons (2 coupons per treatment). The coupons were dried overnight at room temperature in a biological safety cabinet with the lids closed. The initial inoculum suspension was enumerated by plating serial dilutions in duplicate.
  Preparation of the Inocula: The reinoculation suspension was prepared by making $10^{-2}$ and $10^{-4}$ dilutions from an 18-24 hour broth culture of the test system. 5 mL of the $10^{-4}$ dilution was added to 5 mL of Phosphate Buffered Dilution Water (PBDW). A 5% Fetal Bovine Serum (FBS) soil was added to the inoculum suspension, vortexed, and allowed to stand for 15 minutes. The final inoculum suspension was prepared by making $10^{-1}$ dilution from an 18-24 hour culture of the test system, adding 5% FBS, vortexed, and allowed to stand for 15 minutes. Both inoculum suspensions were serially diluted and pour plated in duplicate. The suspensions were not allowed to stand with organic soil for longer than 8 hours.

Operating Technique: 10 wears were performed using the Gardner Abrasion Tester. The wears alternated between dry or wet, beginning with a dry wear and ending with a wet wear. The abrasion boat was assembled in the following manner for each wear: a thin foam pad and a cotton strip were wrapped around the flat surface of the boat. For dry wears, the boat was run over two coupons for one cycle. For wet wears, the boat was sprayed for 1 second with sterile water (in a Prevail sprayer) at a distance of about 75 cm before it was run over two coupons for one cycle. The coupons were reinoculated with 10 μL of the reinoculation suspension, spread evenly and dried at room temperature for 15 to 30 minutes. Coupons were reinoculated after the first 5 wears. Approximately 10 minutes elapsed after the previous wear before the coupons were reinoculated. After the final wear, 10 μL of the final inoculum suspension was spread over the surface of each coupon. At the end of the exposure time of 5 minutes, the coupons were neutralized in 30 mL of D/E Broth in a centrifuge tube. The centrifuge tubes were sonicated for 20 seconds and vortexed vigorously for 1 minute. The tubes were serially diluted and pour plated. As a neutralizer screen, an uninoculated slide was coated with test substance as described in Test Surface Inoculation and Coating and 0.2 mL of a $10^2$ to $10^3$ CFU/mL of test system was added. As a control for the neutralizer screen, an uncoated slide added to the neutralizer and inoculated with test system. The neutralizer screen sat for 30 minutes before pour plating 1 mL and 0.1 mL of the neutralizer Method Parameters:
  Test Substances: Shield Medicare Products:
    Test composition A (Quat/Biguanide a composition of the invention)
    Test composition B (Stabilized Chlorine Dioxide/Quat)
    Biocide A is a ready to use solution of Biguanide and quat on an actives basis of 2000 ppm PHMB and 5000 ppm QAC (ratio of ~1:2.5) It would fall within the intended ranges of the invention
    TritonX-100 A commercially available nonionic detergent from Sigma Chemical, St. Louis Mo. with no antimicrobial activity (control at 0.01%)
  Test Systems: *Staphylococcus aureus* ATCC 6538
    *Klebsiella pneumoniae* ATCC 4352
  Organic Soil: 5% Fetal Bovine Serum
  Test Surface: 1"×1" Glass Surfaces
    1 mm thick non-frosted microscope slides, cut into squares
  Exposure Time: 5 minutes
  Neutralizer
  Medium: 30 mL D/E Broth
    A neutralizer screen showed that this neutralizer provided adequate neutralization and was not detrimental to the test systems.
  Plating Medium: Tryptone Glucose Extract Agar
  Incubation: 35° C. for 48 hours

| | Inoculum Numbers | | | |
|---|---|---|---|---|
| Test System | Culture Description | A | B | Average CFU/mL |
| *Staphylococcus aureus* ATCC 6538 | Initial Inoculum | $48 \times 10^3$ | $53 \times 10^3$ | $5.0 \times 10^4$ |
| | Re-inoculum | $17 \times 10^3$ | $31 \times 10^3$ | $2.4 \times 10^4$ |
| | Final Inoculum | $50 \times 10^6$ | $43 \times 10^6$ | $4.6 \times 10^7$ |

| | *Staphylococcus aureus* ATCC 6538 | | | |
|---|---|---|---|---|
| Test System | Average Survivors (CFU/ Test Surface) | Log of Individual Survivors | Geometric Mean* | Percent Reduction |
| Test Composition A | <30 <br> <30 <br> $3.7 \times 10^3$ | $X_1$: <1.48 <br> $X_2$: <1.48 <br> $X_3$: 3.57 | <$1.5 \times 10^2$ | >99.948 |
| Test Composition B | $1.1 \times 10^5$ <br> $1.4 \times 10^2$ | $X_1$: 2.26 <br> $X_2$: 2.48 <br> $X_3$: 1.95 <br> $X_4$: 1.48 | $3.9 \times 10^3$ | 98.655 |
| TritonX | $3.0 \times 10^5$ <br> $2.0 \times 10^5$ <br> $3.6 \times 10^5$ <br> $3.3 \times 10^5$ | $X_1$: 5.48 <br> $X_2$: 5.30 <br> $X_3$: 5.56 <br> $X_4$: 5.52 | $2.9 \times 10^5$ | N/A |

*[Antilog($X_1 + X_2$)]/2.

| | Inoculum Numbers | | | |
|---|---|---|---|---|
| Test System | Culture Description | A | B | Average CFU/mL |
| *Klebsiella pneumoniae* ATCC 4352 | Inoculum | $47 \times 10^3$ | $62 \times 10^3$ | $5.4 \times 10^4$ |
| | Re-inoculum | $31 \times 10^3$ | $30 \times 10^3$ | $3.0 \times 10^4$ |
| | Final Inoculum | $39 \times 10^6$ | $48 \times 10^6$ | $4.4 \times 10^7$ |

| | *Klebsiella pneumoniae* ATCC 4352 | | | |
|---|---|---|---|---|
| Test Substance | Average Survivors (CFU/ Test Surface) | Log of Individual Survivors | Geometric Mean* | Percent Reduction |
| Test composition A | $7.5 \times 10^1$ <br> $4.5 \times 10^1$ <br> <30 <br> $4.8 \times 10^2$ | $X_1$: 1.88 <br> $X_2$: 1.65 <br> $X_3$: <1.48 <br> $X_4$: 2.68 | $8.4 \times 10^1$ | >99.958 |
| Test Composition B | $1.0 \times 10^5$ <br> $7.1 \times 10^1$ <br> $1.4 \times 10^5$ <br> $2.2 \times 10^5$ | $X_1$: 5.00 <br> $X_2$: 1.85 <br> $X_3$: 5.15 <br> $X_4$: 5.34 | $2.2 \times 10^4$ | 89.000 |
| TritonX | $1.6 \times 10^5$ <br> $2.6 \times 10^5$ <br> $2.7 \times 10^5$ <br> $1.5 \times 10^5$ | $X_1$: 5.20 <br> $X_2$: 5.41 <br> $X_3$: 5.43 <br> $X_4$: 5.18 | $2.0 \times 10^5$ | N/A |

*[Antilog($X_1 + X_2$)]/2.

Conclusion:

To be defined as a sanitizer, the test substances on the hard inanimate surface must reduce the total number of organisms by at least 99.9% (based on the Geometric Mean) on the surface within a 5 minute period (after the final inoculation).

Against *S. aureus* and *K. pneumoniae*, Test Composition A achieved the required minimum percent reduction on the hard inanimate surface within the specified exposure time, and Test Composition B did not.

Example 2

Residual Self-Sanitizing Screen of Test Composition A

The objective of the analysis was to examine the residual self-sanitizing efficacy of against *Staphylococcus aureus* ATCC 6538 and *Klebsiella pneumoniae* ATCC 4352 after application to inanimate, non-porous, non-food contact surfaces.

Test Method:

Residual Self-Sanitizing Activity on Hard, Non-Porous Surfaces

Test System Preparation

1. At least three consecutive loop transfers of a 24 hour culture of *Staphylococcus aureus* ATCC 6538 and *Klebsiella pneumoniae* ATCC 4352 were performed in 10 mL of AOAC Synthetic broth or AOAC Nutrient broth (respectively) and incubated at 35° C.
2. Initial Inoculum Suspension:
   2.1 Vortex a 48-54 hour culture for 3-4 seconds.
   2.2 Make two 1/100 dilutions in sterile PBDW and let stand for 151 minutes.
3. Reinoculation Suspension:
   3.1 Vortex an 18-24 hour culture for 3-4 seconds.
   3.2 Make two 1/100 dilutions in sterile PBDW and on final dilution of 5.0 mL of diluted culture in 5.0 mL of sterile PBDW.
   3.3 Add organic coil load to equal 5%, vortex, and let stand for 151 minutes.
4. Final Inoculum Suspension:
   4.1 Vortex an 18-24 hour culture for 3-4 seconds.
   4.2 Make one 1/10 dilution in sterile PBDW and vortex.
   4.3 Add organic soil load to equal 5%, vortex, and let stand for 151 minutes.

Test Surface Preparation

1. Clean glass surfaces by rinsing in alcohol, then sterile water, and allow to air dry.
2. Decontaminate glass surfaces by immersing in absolute ethanol and allowing to air dry (slides can be autoclaved if necessary).
3. Transfer to individual glass petri dishes lined with 1-2 layers of sterile Whatman No. 2 paper, and allow all surfaces to dry completely prior to use (approximately one day).
4. Inoculation of Test Surfaces
   4.1. Apply a 10 µL aliquot of the Initial Inoculum Suspension (Step 2 in the Test System Preparation) to each of 2-4 prepared test surfaces, per test substance, per test system. Also inoculate 2-4 prepared test surfaces, per test system, to be used as control surfaces.
   4.2. Spread inoculum to within ⅛ inch of the edge with the pipette tip.
   4.3. Dry with lids cracked at 35° C. for 30-35 minutes, or until visibly dry.
   4.4. Apply the test substance to the test surfaces on a clean dry surface. Apply test substance to each test surface appropriate to the application instructions. If no application method is specified, apply 50 µL of the test substance to the test surface and spread, with a sterile disposable loop, in an even layer over entire test surface. Allow the surfaces to dry overnight, covered, at room temperature.
5. Apply a 0.01% TritonX 100 solution (made and filter sterilized on the day of application) to each of the control surfaces in the same manner as the test substances. Allow the control surfaces to dry under the same conditions as the test surfaces.

Operating Technique

1. Wear and Reinoculation of Test and Control Surfaces: The treated surfaces will undergo a wear and reinoculation regimen, which will take place over at least a 24 hour period at room temperature.
2. GardCo Washability and Wear Tester: A cycle equals one pass to the left, and a return pass to the right. One pass on the abrasion tester should provide a contact time with the surfaces of approximately 2 seconds.
3. Place one set of surfaces (two test or control surfaces) into the cut out region of the surface wear area on the abrasion tester, and perform one cycle of surface wears.
4. Decontaminate the surface wear area with absolute ethanol between each set of surface wears to prevent carry-over contamination. Allow the alcohol to completely evaporate before proceeding. Replace the foam liner and the cotton cloth, on the abrasion boat assembly, between each set of surface wears.
5. Alternate dry-wears and wet-wears. For wet-wears, spray clean cotton cloth with sterile distilled water, using a Preval sprayer, from a distance of 75±1 cm for not more than one second. Immediately attach the moistened abrasion boat assembly to the abrasion tester, and perform one cycle of surface wears.
6. Wait at least 15 minutes after each wear to reinoculate surfaces. Reinoculate test and control surfaces by applying 10 µL of the Reinoculation Suspension (Step 3 in Test System Preparation) and spread the inoculum to within ⅛ inch of the surface edge with a the pipette tip. Dry at least 30 minutes at room temperature before proceeding with the next wear.
7. The period between test substance application and the initiation of the sanitizer test (carriers into neutralizer broth) must be at least 24 hours.

Enumeration of Survivors

1. With the Final Inoculum Suspension (Step 4 in Test System Preparation), inoculate the first surface with 10 µL, at time zero. Begin inoculation about 5 seconds before time zero, and spread aliquot over the surface so it is completed at time zero. Begin the inoculation of the second surface similarly, at given intervals, until all test and control surfaces have been inoculated.
2. At 5 minutes (or other appropriate time) use alcohol-flamed forceps to transfer the surfaces to 30 mL of neutralizer broth in a 50 mL centrifuge tube. Repeat until all test and control surfaces have been completed.
3. Sonicate the samples for 20±2 seconds in a sonicating water bath. Then agitate the samples on an orbital shaker for 3-4 minutes at 250 rpm.
4. Serially dilute the control sample suspensions in PBDW and prepare duplicate pour plates of the $10^{-2}$, $10^{-3}$ and $10^{-4}$ dilutions. The control plates must have a minimum of $1\times10^4$ CFU/mL for a valid test.
5. Serially dilute the test sample suspensions in PBDW and prepare duplicate pour plates of the $10^0$, $10^{-2}$ and $10^{-4}$ dilutions.
6. Plate all samples within 30 minutes of their transfer to neutralizer broth.

Method Parameters:
Test Substance Formula:

| Test composition A | | |
|---|---|---|
| Raw Material | Manufacturer | Concentration |
| Bardac 2250 (50% active Quaternary ammonium compound) | Lonza | 1.0% |
| Vantocil P (20% Biguanide) | Arch Chemicals | 1.0% |
| Distilled Water | | 98% |

Test Systems: *Staphylococcus aureus* ATCC 6538
   *Klebsiella pneumoniae* ATCC 4352
Soil Challenge: 5% Bovine Serum
Test Material: 1"×1" Glass Surfaces
   1 mm thick non-frosted microscope slides, cut into squares
Test Substance Application: 3 sprays applied with a sprayer
Initial Inoculum Application Time: 2:30 pm (Sep. 8, 2008)
Test Substance Application Time: 2:45 pm (Sep. 8, 2008)
Final Inoculum Application Time: 3:05 pm (Sep. 9, 2008)
Neutralizer Medium: 30 mL Dey Engley Broth
   A neutralizer screen was performed as part of the testing, verified that the neutralizer adequately neutralized the product and was not detrimental to the tested organisms.
Plating Medium: Tryptone Glucose Extract Agar
Incubation: 35° C. for 48 hours

| Inoculum Numbers | | | | |
|---|---|---|---|---|
| Test System | Inoculum Suspension | A | B | Average CFU/mL |
| *Staphylococcus aureus* ATCC 6538 | Initial | $113 \times 10^3$ | $84 \times 10^3$ | $9.8 \times 10^4$ |
| | Reinoculation | $61 \times 10^3$ | $53 \times 10^3$ | $5.7 \times 10^4$ |
| | Final | $139 \times 10^6$ | $132 \times 10^6$ | $1.4 \times 10^8$ |
| *Klebsiella pneumoniae* ATCC 4352 | Initial | $81 \times 10^3$ | $62 \times 10^3$ | $7.2 \times 10^4$ |
| | Reinoculation | $60 \times 10^3$ | $54 \times 10^3$ | $5.7 \times 10^4$ |
| | Final | $100 \times 10^6$ | $120 \times 10^7$ | $1.1 \times 10^8$ |

| *Staphylococcus aureus* ATCC 6538 | | | | |
|---|---|---|---|---|
| Test Substance | Survivors (CFU/mL) | Survivors (CFU/Carrier)* | Average CFU/Carrier | Percent Reduction |
| TritonX | $96 \times 10^2$, $105 \times 10^2$ $119 \times 10^2$, $200 \times 10^2$ | $2.9 \times 10^5$, $3.2 \times 10^5$ $3.6 \times 10^5$, $6.0 \times 10^5$ | $3.9 \times 10^5$ | N/A |
| Test Composition A | $0 \times 10^0$, $0 \times 10^0$ $0 \times 10^0$, $0 \times 10^0$ | <30, <30, <30, <30 | <30 | >99.992 |

*CFU/mL × 30

| *Klebsiella pneumoniae* ATCC 4352 | | | | |
|---|---|---|---|---|
| Test Substance | Survivors (CFU/mL) | Survivors (CFU/Carrier)* | Average CFU/Carrier | Percent Reduction |
| TritonX | $149 \times 10^2$, $153 \times 10^2$ $152 \times 10^2$, $148 \times 10^2$ | $4.5 \times 10^5$, $4.6 \times 10^5$ $4.6 \times 10^5$, $4.4 \times 10^5$ | $4.5 \times 10^5$ | N/A |
| Test Composition A | $2 \times 10^0$, $2 \times 10^0$ $0 \times 10^0$, $0 \times 10^0$ | $6.0 \times 10^1$, $6.0 \times 10^1$ <30, <30 | $<4.5 \times 10^1$ | >99.990 |

*CFU/mL × 30

Conclusion:
   To be defined as a sanitizer, the test substances on the hard inanimate surface must reduce the total number of organisms by at least 99.9% (based on the Geometric Mean) on the surface within a 5 minute period (after the final inoculation).
   Test composition A passed the residual hard surface sanitizer screen with a 5 minute final exposure, against *S. aureus* and *K. pneumoniae*.

Example 3

Residual Self-Sanitizing Screen of Test Composition C

The objective of the analysis was to examine the residual self-sanitizing efficacy of Test composition C (a composition according to the invention) against *Staphylococcus aureus* ATCC 6538 and *Klebsiella pneumoniae* ATCC 4352 after application to inanimate, non-porous, non-food contact surfaces.

Test Method:
Residual Self-Sanitizing Activity on Hard, Non-Porous Surfaces
Test System Preparation
1. At least three consecutive loop transfers of a 24 hour culture of *Staphylococcus aureus* ATCC 6538 and *Klebsiella pneumoniae* ATCC 4352 were performed in 10 mL of AOAC Synthetic broth or AOAC Nutrient broth (respectively) and incubated at 35° C.
2. Initial Inoculum Suspension:
   2.1 Vortex a 48-54 hour culture for 3-4 seconds.
   2.2 Make two 1/100 dilutions in sterile PBDW and let stand for 151 minutes.
3. Reinoculation Suspension:
   3.1 Vortex an 18-24 hour culture for 3-4 seconds.
   3.2 Make two 1/100 dilutions in sterile PBDW and on final dilution of 5.0 mL of diluted culture in 5.0 mL of sterile PBDW.
   3.3 Add organic coil load to equal 5%, vortex, and let stand for 151 minutes.
4. Final Inoculum Suspension:
   4.1 Vortex an 18-24 hour culture for 3-4 seconds.
   4.2 Make one 1/10 dilution in sterile PBDW and vortex.
   4.3 Add organic soil load to equal 5%, vortex, and let stand for 151 minutes.
Test Surface Preparation
1. Clean glass surfaces by rinsing in alcohol, then sterile water, and allow to air dry.
2. Decontaminate glass surfaces by immersing in absolute ethanol and allowing to air dry (slides can be autoclaved if necessary).
3. Transfer to individual glass petri dishes lined with 1-2 layers of sterile Whatman No. 2 paper, and allow all surfaces to dry completely prior to use (approximately one day).
4. Inoculation of Test Surfaces
   4.1. Apply a 10 μL aliquot of the Initial Inoculum Suspension (Step 2 in the Test System Preparation) to each of 2-4 prepared test surfaces, per test substance, per test system. Also inoculate 2-4 prepared test surfaces, per test system, to be used as control surfaces.
   4.2. Spread inoculum to within ⅛ inch of the edge with the pipette tip.
   4.3. Dry with lids cracked at 35° C. for 30-35 minutes, or until visibly dry.
   4.4. Apply the test substance to the test surfaces on a clean dry surface. Apply test substance to each test surface appropriate to the application instructions. If no application method is specified, apply 50 μL of the test substance to the test surface and spread, with a sterile disposable loop, in an even layer over entire test surface. Allow the surfaces to dry overnight, covered, at room temperature.
5. Apply a 0.01% TritonX 100 solution (made and filter sterilized on the day of application) to each of the control surfaces in the same manner as the test substances. Allow the control surfaces to dry under the same conditions as the test surfaces.
Operating Technique
1. Wear and Reinoculation of Test and Control Surfaces: The treated surfaces will undergo a wear and reinoculation regimen, which will take place over at least a 24 hour period at room temperature.
2. GardCo Washability and Wear Tester: A cycle equals one pass to the left, and a return pass to the right. One pass on the abrasion tester should provide a contact time with the surfaces of approximately 2 seconds.
3. Place one set of surfaces (two test or control surfaces) into the cut out region of the surface wear area on the abrasion tester, and perform one cycle of surface wears.
4. Decontaminate the surface wear area with absolute ethanol between each set of surface wears to prevent carry-over contamination. Allow the alcohol to completely evaporate before proceeding. Replace the foam liner and the cotton cloth, on the abrasion boat assembly, between each set of surface wears.
5. Alternate dry-wears and wet-wears. For wet-wears, spray clean cotton cloth with sterile distilled water, using a Preval sprayer, from a distance of 75±1 cm for not more than one second. Immediately attach the moistened abrasion boat assembly to the abrasion tester, and perform one cycle of surface wears.
6. Wait at least 15 minutes after each wear to reinoculate surfaces. Reinoculate test and control surfaces by applying 10 μL of the Reinoculation Suspension (Step 3 in Test System Preparation) and spread the inoculum to within ⅛ inch of the surface edge with a the pipette tip. Dry at least 30 minutes at room temperature before proceeding with the next wear.
7. The period between test substance application and the initiation of the sanitizer test (carriers into neutralizer broth) must be at least 24 hours.

Enumeration of Survivors
1. With the Final Inoculum Suspension (Step 4 in Test System Preparation), inoculate the first surface with 10 μL, at time zero. Begin inoculation about 5 seconds before time zero, and spread aliquot over the surface so it is completed at time zero. Begin the inoculation of the second surface similarly, at given intervals, until all test and control surfaces have been inoculated.
2. At 5 minutes (or other appropriate time) use alcohol-flamed forceps to transfer the surfaces to 30 mL of neutralizer broth in a 50 mL centrifuge tube. Repeat until all test and control surfaces have been completed.
3. Sonicate the samples for 20±2 seconds in a sonicating water bath. Then agitate the samples on an orbital shaker for 3-4 minutes at 250 rpm.
4. Serially dilute the control sample suspensions in PBDW and prepare duplicate pour plates of the $10^{-2}$, $10^{-3}$ and $10^{-4}$ dilutions. The control plates must have a minimum of $1 \times 10^4$ CFU/mL for a valid test.
5. Serially dilute the test sample suspensions in PBDW and prepare duplicate pour plates of the $10^0$, $10^{-2}$ and $10^{-4}$ dilutions.
6. Plate all samples within 30 minutes of their transfer to neutralizer broth.

Method Parameters:
Test Substance Formula:

| Test composition C | |
| --- | --- |
| Raw Material | Concentration |
| Bardac DM50 (Alkyl benzyl quat 50% active)) | 50% |
| Vantocil P (PHMG 20% active) | 50% |

Test Substance Dilutions:

| Prepared on Jan. 20, 2009: | | |
|---|---|---|
| Desired Concentration | Diluent | Test Solution (Volume of Test Substance/Total Volume) |
| 1:64 | 410 ppm Synthetic Hard Water (pH 7.65) | 1.56 mL/100 mL |
| 1:64 | 510 ppm Synthetic Hard Water (pH 7.84) | 1.56 mL/100 mL |

Test Systems: *Staphylococcus aureus* ATCC 6538
    *Klebsiella pneumoniae* ATCC 4352
    *Staphylococcus aureus* (MRSA) ATCC 33592
    *Enterococcus faecalis* (VRE) ATCC 51299
Soil Challenge: 5% Bovine Serum
Test Material: 1"×1" Glass Surfaces
    1 mm thick non-frosted microscope slides, cut into squares
Test Substance Application: 50 µL applied and spread end to end with a pipette tip
Number of Wears Performed: 12 Total (6 dry and 6 wet)
Number of Re-inoculations Performed: 5 Total
Neutralizer Medium: 30 mL Dey Engley Broth
    A neutralizer screen was performed as part of the testing, verified that the neutralizer adequately neutralized the product and was not detrimental to the tested organisms.
Plating Medium: Tryptone Glucose Extract Agar
Incubation: 35° C. for 48 hours

| Inoculum Numbers | | | | |
|---|---|---|---|---|
| Test System | Inoculum Suspension | A | B | Average CFU/mL |
| MRSA ATCC 33592 | Initial | $148 \times 10^3$ | $155 \times 10^3$ | $1.5 \times 10^5$ |
| | Reinoculation | $61 \times 10^3$ | $45 \times 10^3$ | $5.3 \times 10^4$ |
| | Final | $124 \times 10^6$ | $134 \times 10^6$ | $1.3 \times 10^8$ |
| VRE ATCC 51299 | Initial | $34 \times 10^4$ | $35 \times 10^4$ | $3.5 \times 10^5$ |
| | Reinoculation | $94 \times 10^3$ | $136 \times 10^3$ | $1.2 \times 10^5$ |
| | Final | $50 \times 10^7$ | $35 \times 10^7$ | $4.2 \times 10^8$ |

| MRSA ATCC 33592 | | | | |
|---|---|---|---|---|
| Test Substance | Survivors (CFU/mL) | Survivors (CFU/Carrier)* | Average CFU/Carrier | Percent Reduction |
| TritonX | $253 \times 10^2$, $263 \times 10^2$ $268 \times 10^2$, $251 \times 10^2$ | $7.59 \times 10^5$, $7.89 \times 10^5$ $8.04 \times 10^5$, $7.53 \times 10^5$ | $7.8 \times 10^5$ | N/A |
| Test Composition C | $0 \times 10^0$, $0 \times 10^0$ $0 \times 10^0$, $1 \times 10^0$ | <30, <30, <30, $3.00 \times 10^1$ | <30 | >99.996 |

*CFU/mL × 30

| VRE ATCC 51299 | | | | |
|---|---|---|---|---|
| Test Substance | Survivors (CFU/mL) | Survivors (CFU/Carrier)* | Average CFU/Carrier | Percent Reduction |
| TritonX | $67 \times 10^3$, $90 \times 10^3$ $67 \times 10^3$, $66 \times 10^3$ | $2.01 \times 10^6$, $2.70 \times 10^6$ $2.01 \times 10^6$, $1.98 \times 10^6$ | $2.2 \times 10^6$ | N/A |
| Test Composition C | $4 \times 10^2$, $4 \times 10^2$ $0 \times 10^0$, $0 \times 10^0$ | $1.20 \times 10^4$, $1.20 \times 10^4$ <30, <30 | $<6.0 \times 10^3$ | >99.727 |

*CFU/mL × 30

Test Date: Jan. 22, 2009
Date Results Read: Jan. 26, 2009

| Inoculum Numbers | | | | |
|---|---|---|---|---|
| Test System | Inoculum Suspension | A | B | Average CFU/mL |
| *Staphylococcus aureus* ATCC 6538 | Initial | $114 \times 10^3$ | $100 \times 10^3$ | $1.1 \times 10^5$ |
| | Reinoculation | $43 \times 10^3$ | $55 \times 10^3$ | $4.9 \times 10^4$ |
| | Final | $111 \times 10^6$ | $112 \times 10^6$ | $1.1 \times 10^8$ |
| *Klebsiella pneumonias* ATCC 4352 | Initial | $117 \times 10^3$ | $142 \times 10^3$ | $1.3 \times 10^5$ |
| | Reinoculation | $55 \times 10^3$ | $60 \times 10^3$ | $5.8 \times 10^4$ |
| | Final | $109 \times 10^7$ | $129 \times 10^7$ | $1.2 \times 10^9$ |

| Staphylococcus aureus ATCC 6538 | | | | |
|---|---|---|---|---|
| Test Substance | Survivors (CFU/mL) | Survivors (CFU/Carrier)* | Average CFU/Carrier | Percent Reduction |
| TritonX | $30 \times 10^3$, $19 \times 10^3$ $31 \times 10^3$, $26 \times 10^3$ | $9.00 \times 10^5$, $5.70 \times 10^5$ $9.30 \times 10^5$, $7.80 \times 10^5$ | $8.0 \times 10^5$ | N/A |
| Test Composition C | $0 \times 10^0$, $0 \times 10^0$ $0 \times 10^0$, $0 \times 10^0$ | <30, <30, <30, <30 | <30 | >99.996 |

*CFU/mL × 30

| Klebsiella pneumoniae ATCC 4352 | | | | |
|---|---|---|---|---|
| Test Substance | Survivors (CFU/mL) | Survivors (CFU/Carrier)* | Average CFU/Carrier | Percent Reduction |
| TritonX | $22 \times 10^3$, $18 \times 10^3$ $48 \times 10^2$, $75 \times 10^2$ | $6.60 \times 10^5$, $5.40 \times 10^5$ $1.44 \times 10^5$, $2.25 \times 10^5$ | $3.9 \times 10^5$ | N/A |
| Test Composition C | $0 \times 10^0$, $0 \times 10^0$ $0 \times 10^0$, $0 \times 10^0$ | <30, <30, <30, <30 | <30 | >99.992 |

*CFU/mL × 30

Conclusion:

To be defined as a sanitizer, the test substances on the hard inanimate surface must reduce the total number of organisms by at least 99.9% on the surface within a 5 minute period (after the final inoculation).

Test Composition C passed with a greater than 99.9% reduction in S. aureus, K. pneumoniae and MRSA numbers, and almost passed against VRE with a greater than 99.7% reduction.

Example 4

Residual Hard Surface Virucidal Efficacy of Test Composition C

The objective of this analysis was to examine the virucidal efficacy of Biocide X, a residual product according to the invention), against Herpes Simplex I virus after application to inanimate, non-porous, non-food contact surfaces. A test method was developed based on the Residual Self-Sanitizing Activity on Hard, Non-Porous Surfaces method, but adapted for viruses.

Test Method:
Residual Self-Virucidal Activity on Hard, Non-Porous Surfaces

Test Surface Preparation:
Clean glass test surfaces were sterilized in an autoclave. The test surfaces were placed in sterile glass petri dishes containing 2 layers of Whatman No. 2 paper. Each petri dish had two coupons in them.

Test Surface Inoculation and Coating:
10 μL of thawed viral stock was spread evenly over the entire coupon. The coupons were dried at ambient temperature for 30 minutes with the lids cracked open. 50 μL of the test substance was spread evenly onto the coupons, and 50 μL of 0.01% Triton X 100 was gently spread over the surface of the control coupons (2 coupons per treatment). The coupons were dried overnight at ambient temperature in a biological safety cabinet with the lids closed.

Operating Technique:
12 wears were performed using the Gardner Abrasion Tester. The wears alternated between dry or wet, beginning with a dry wear and ending with a wet wear. The abrasion boat was assembled in the following manner for each wear: a thin foam pad and a cotton strip were wrapped around the flat surface of the boat. For dry wears, the boat was run over two coupons for one cycle. For wet wears, the boat was sprayed for 1 second with sterile water (in a Prevail sprayer) at a distance of about 75 cm before it was run over two coupons for one cycle. The coupons were reinoculated with 10 μL of thawed viral stock (stock was refrigerated when not in use), spread evenly and dried at ambient temperature until visibly dry. Coupons were reinoculated after the first 5 wears. Approximately 5 minutes elapsed after the previous wear before the coupons were reinoculated. After the final wear, 10 μL of a new viral stock was spread over the surface of each coupon. After 9 minutes of exposure, 200 μL of cell culture medium was place on top of each coupon and scraped with a cell scraper. At the end of the exposure time of 10 minutes, 100 μL of the scraped cells/cell culture medium were added to a prepared GE column and centrifuged for 1 minute, and then added to 900 μL of Fetal Bovine Serum (10.2 dilution). Each coupon was serially diluted in cell culture medium and added to prepared 24 well cell culture plates seeded with the appropriate cell line for the virus tested. The plates were examined for Cytopathic Effects (CPE) after 7 days of incubation at 35±2° C. with 5% $CO_2$.

Method Parameters:
Test Substance: Test Composition C
Virus: Herpes Simplex 1
Cell Line: Vero Cells
Number of Wears: 12
Test Surface: 1 inch×1 inch square glass slides
Organic Soil: 5% Fetal Bovine Serum (FBS)
Final Inoculum Exposure Time: 10 minutes
Exposure Temperatures: Ambient
Neutralizer: GE Sephacryl & Fetal Bovine Serum
Cell Culture Media: Eagle's Minimum Essential Medium (EMEM) with 5% Fetal Bovine Serum
Incubation: 7 days at 35±2° C., 5% $CO_2$ Results:

| Dilution | Virus Control Rep 1* | Virus Control Rep 2* | Test Composition C Residual Rep 1 | Test Composition C Residual Rep 2 |
|---|---|---|---|---|
| Cell Control | 0 0 0 0 | 0 0 0 0 | 0 0 0 0 | 0 0 0 0 |
| $10^{-2}$ | + + + + | + + + + | 0 0 0 0 | 0 0 0 0 |
| $10^{-3}$ | + + + + | + + + + | 0 0 0 0 | 0 0 0 0 |
| $10^{-4}$ | 0 + + 0 | + + + + | 0 0 0 0 | 0 0 0 0 |
| $10^{-5}$ | 0 0 0 0 | + + 0 0 | 0 0 0 0 | 0 0 0 0 |
| $10^{-6}$ | 0 0 0 0 | 0 0 0 0 | 0 0 0 0 | 0 0 0 0 |
| $TCID_{50}/0.1$ mL | $10^{4.0}$ | $10^{5.0}$ | $\leq 10^{1.5}$ | $\leq 10^{1.5}$ |
| $Log_{10}$ Reduction | | | $\geq 3.0$ | $\geq 3.0$ |

*Results averaged ($10^{4.5}$) and used to calculate the $Log_{10}$ Reduction

| Dilution | Test Composition C Neutralizer | Test Composition C Cytotoxicity |
|---|---|---|
| Cell Control | 0 0 | 0 0 |
| $10^{-2}$ | + + | 0 0 |
| $10^{-3}$ | + + | 0 0 |
| $10^{-4}$ | + 0 | 0 0 |
| $10^{-5}$ | + + | 0 0 |
| $10^{-6}$ | 0 0 | 0 0 |

+ = Positive for the presence of the test virus
0 = Negative for the presence of the virus and/or no cytotoxicity present Conclusion:

The average of the viral titer in this test was $10^{4.5}$, and Test Composition C Residual showed complete inactivation of the Herpes Simplex 1 virus for a log reduction of $\geq 3.0$. While there are no specific standards for effective Residual Self-Virucidal products/claims, these test results would meet the current hard surface virucidal standards.

Example 5

100-Wear Residual Hard Surface Screen of Test Composition C

Objective:

The objective of the analysis was to examine the residual hard surface efficacy of Test Composition C against *Staphylococcus aureus* ATCC 6538 and *Klebsiella pneumoniae* ATCC 4352 after application to inanimate, non-porous, non-food contact surfaces.

Test Method:

Residual Self-Sanitizing Activity on Hard, Non-Porous Surfaces

Test System Preparation

1. At least three consecutive loop transfers of a 24 hour culture of *Staphylococcus aureus* ATCC 6538 and *Klebsiella pneumoniae* ATCC 4352 were performed in 10 mL of AOAC Synthetic broth or AOAC Nutrient broth (respectively) and incubated at 35° C.
2. Final Inoculum Suspension:
   2.1. Vortex an 18-24 hour culture for 3-4 seconds.
   2.2. Make one 1/10 dilution in sterile PBDW and vortex.
   2.3. Add organic soil load to equal 5%, vortex, and let stand for 151 minutes.

Test Surface Preparation

1. Clean glass surfaces by rinsing in alcohol, then sterile water, and allow to air dry.
2. Decontaminate glass surfaces by immersing in absolute ethanol and allowing to air dry (slides can be autoclaved if necessary).
3. Transfer to individual glass petri dishes lined with 1-2 layers of sterile Whatman No. 2 paper, and allow all surfaces to dry completely prior to use (approximately one day).
4. Apply the test substance to the test surfaces on a clean dry surface. Apply test substance to each test surface appropriate to the application instructions. If no application method is specified, apply 50 µL of the test substance to the test surface and spread, with a sterile disposable loop, in an even layer over entire test surface. Allow the surfaces to dry overnight, covered, at room temperature.
5. Apply a 0.01% TritonX 100 solution (made and filter sterilized on the day of application) to each of the control surfaces in the same manner as the test substances. Allow the control surfaces to dry under the same conditions as the test surfaces.

Operating Technique

1. Wear and Reinoculation of Test and Control Surfaces: The treated surfaces will undergo a wear and reinoculation regimen, which will take place over at least a 24 hour period at room temperature.
2. GardCo Washability and Wear Tester: A cycle equals one pass to the left, and a return pass to the right. One pass on the abrasion tester should provide a contact time with the surfaces of approximately 2 seconds.
3. Place one set of surfaces (two test or control surfaces) into the cut out region of the surface wear area on the abrasion tester, and perform 100 cycles of surface wears.
4. Decontaminate the surface wear area with absolute ethanol between each set of surface wears to prevent carry-over contamination. Allow the alcohol to completely evaporate before proceeding. Replace the foam liner and the cotton cloth, on the abrasion boat assembly, between each set of surface wears.
5. The period between test substance application and the initiation of the sanitizer test (carriers into neutralizer broth) must be at least 24 hours.

Enumeration of Survivors

1. With the Final Inoculum Suspension (Step 2 in Test System Preparation), inoculate the first surface with 10 µL, at time zero. Begin inoculation about 5 seconds before time zero, and spread aliquot over the surface so it is completed at time zero. Begin the inoculation of the second surface similarly, at given intervals, until all test and control surfaces have been inoculated.
2. At 5 minutes (or other appropriate time) use alcohol-flamed forceps to transfer the surfaces to 30 mL of neutralizer broth in a 50 mL centrifuge tube. Repeat until all test and control surfaces have been completed.
3. Sonicate the samples for 20±2 seconds in a sonicating water bath. Then agitate the samples on an orbital shaker for 3-4 minutes at 250 rpm.
4. Serially dilute the control sample suspensions in PBDW and prepare duplicate pour plates of the $10^{-2}$, $10^{-3}$ and $10^{-4}$ dilutions. The control plates must have a minimum of $1 \times 10^4$ CFU/mL for a valid test.
5. Serially dilute the test sample suspensions in PBDW and prepare duplicate pour plates of the $10^0$, $10^{-2}$ and 10-4 dilutions.
6. Plate all samples within 30 minutes of their transfer to neutralizer broth.

Method Parameters:
Test Substance Formula:

| Test composition C | |
|---|---|
| Raw Material | Concentration |
| Bardac DM50 (Alkyl benzyl quat 50% active)) | 50% |
| Vantocil P (PHMG 20% active) | 50% |

Test Systems: *Staphylococcus aureus* ATCC 6538
  *Klebsiella pneumoniae* ATCC 4352
Soil Challenge: 5% Bovine Serum
Test Material: 1"×1" Glass Surfaces
  1 mm thick non-frosted microscope slides, cut into squares
Test Substance Application: 50 μL applied and spread end to end with a pipette tip—wiped on with a soft cloth
Number of Wears Performed: 100 per slide set
Number of Re-inoculations Performed: None Neutralizer Medium: 20 mL Dey Engley Broth A neutralizer screen was performed as part of the testing, verified that the neutralizer adequately neutralized the product and was not detrimental to the tested organisms.
Plating Medium: Tryptone Glucose Extract Agar
Incubation: 35° C. for 48 hours

| Inoculum Numbers | | | | |
|---|---|---|---|---|
| Test System | Inoculum Suspension | A | B | Average CFU/mL |
| *Staphylococcus aureus* ATCC 6538 | Final | $83 \times 10^6$ | $84 \times 10^6$ | $8.4 \times 10^7$ |
| *Klebsiella pneumoniae* ATCC 4352 | Final | $102 \times 10^6$ | $86 \times 10^6$ | $9.4 \times 10^7$ |

| *Staphylococcus aureus* ATCC 6538 | | | | | | |
|---|---|---|---|---|---|---|
| Test Substance | Rep | CFU/mL | CFU/Carrier* | Average Log Growth | Geometric Mean | Percent Reduction |
| Triton X | 1 | $36 \times 10^3$ | $7.20 \times 10^5$ | 5.76 | $5.8 \times 10^5$ | N/A |
|  |  | $21 \times 10^3$ | $4.20 \times 10^5$ |  |  |  |
| Test composition C (pipette application) | 1 | $138 \times 10^2$ | $2.76 \times 10^5$ | 5.42 | $3.6 \times 10^5$ | 37.931 |
|  |  | $123 \times 10^2$ | $2.46 \times 10^5$ |  |  |  |
|  | 2 | $251 \times 10^2$ | $5.02 \times 10^5$ | 5.69 |  |  |
|  |  | $243 \times 10^2$ | $4.86 \times 10^5$ |  |  |  |
| Test composition C (wipe application) | 1 | $362 \times 10^2$ | $7.24 \times 10^5$ | 5.82 | $7.1 \times 10^5$ | 0.000 |
|  |  | $293 \times 10^2$ | $5.86 \times 10^5$ |  |  |  |
|  | 2 | $367 \times 10^2$ | $7.34 \times 10^5$ | 5.88 |  |  |
|  |  | $386 \times 10^2$ | $7.72 \times 10^5$ |  |  |  |

*Average CFU/mL × Total Volume of Neutralized Test Substance (20 mL).

| *Klebsiella pneumoniae* ATCC 4352 | | | | | | |
|---|---|---|---|---|---|---|
| Test Substance | Rep | CFU/mL | CFU/Carrier* | Average Log Growth | Geometric Mean | Percent Reduction |
| Triton X | 1 | $37 \times 10^3$ | $7.40 \times 10^5$ | 5.84 | $6.9 \times 10^5$ | N/A |
|  |  | $32 \times 10^3$ | $6.40 \times 10^5$ |  |  |  |
| Test composition C (pipette application) | 1 | $189 \times 10^2$ | $3.78 \times 10^5$ | 5.60 | $3.8 \times 10^5$ | 44.928 |
|  |  | $205 \times 10^2$ | $4.10 \times 10^5$ |  |  |  |
|  | 2 | $186 \times 10^2$ | $3.72 \times 10^5$ | 5.55 |  |  |
|  |  | $171 \times 10^2$ | $3.42 \times 10^5$ |  |  |  |
| Test composition C (wipe application) | 1 | $235 \times 10^2$ | $4.70 \times 10^5$ | 5.67 | $4.5 \times 10^5$ | 34.783 |
|  |  | $238 \times 10^2$ | $4.76 \times 10^5$ |  |  |  |
|  | 2 | $215 \times 10^2$ | $4.30 \times 10^5$ | 5.63 |  |  |
|  |  | $214 \times 10^2$ | $4.28 \times 10^5$ |  |  |  |

*Average CFU/mL × Total Volume of Neutralized Test Substance (20 mL).

Conclusion:

To be defined as a sanitizer, the test substance on the hard inanimate surface must reduce the total number of organisms by at least 99.9% (based on the Geometric Mean) on the surface with a 5 minute period (after the final inoculation).

None of the Test composition C samples (pipette application and wipe application passed the 100 wear screen, against *S. aureus* or *K. pneumoniae*, after a 5 minute final exposure.

Example 6

Residual Self-Sanitizing Screen of Test Composition C in a Concentration Gradient Objective:

The objective of the analysis was to examine the residual self-sanitizing efficacy of Test composition C in a concentration gradient against *Staphylococcus aureus* ATCC 6538 and *Klebsiella pneumonia* ATCC 4352 after application to inanimate, non-porous, non-food contact surfaces.

Test Method:

Residual Self-Sanitizing Activity on Hard, Non-Porous Surfaces

Test System Preparation
1. At least three consecutive loop transfers of a 24 hour culture of *Staphylococcus aureus* ATCC 6538 and *Klebsiella pneumoniae* ATCC 4352 were performed in 10 mL of AOAC Synthetic broth of AOAC Nutrient broth (respectively) and incubated at 35° C.
2. Initial Inoculum Suspension:
   2.1 Vortex a 48-54 hour culture for 3-4 seconds.
   2.2 Make two 1/100 dilutions in sterile PBDW and let stand for 151 minutes.
3. Final Inoculum Suspension:
   3.1 Vortex an 18-24 hour culture for 3-4 seconds.
   3.2 Make one 1/10 dilution in sterile PBDW and vortex.
   3.3 Add organic soil load to equal 5%, vortex, and let stand for 151 minutes.

Test Surface Preparation
1. Test surfaces were cleaned and autoclaved glass coverslips.
2. Inoculation of Test Surfaces
   2.1 Apply a 10 µL aliquot of the Initial Inoculum Suspension (Step 2 in the Test System Preparation) to each of 2-4 prepared test surfaces, per test substance, per test system. Also inoculate 2-4 prepared test surfaces, per test system, to be used as control surfaces.
   2.2 Spread inoculum to within ⅛ inch of the edge with the pipette tip.
   2.3 Dry with lids cracked at 35° C. for 30-35 minutes, or until visibly dry.
   2.4 Apply the test substance to the test surfaces on a clean dry surface. Apply test substance to each test surface appropriate to the application instructions. If no application method is specified, apply 50 µL of the test substance to the test surface and spread, with a sterile disposable lop, in an even layer over entire test surface. Allow the surface to dry overnight, covered, at room temperature.
3. Apply a 0.01% TritonX 100 solution (made and filter sterilized on the day of application) to each of the control surfaces in the same manner as the test substances. Allow the control surfaces to dry under the same conditions as the test surfaces.

Operating Technique
1. The period between test substance application and the initiation of the sanitizer test (carriers into neutralizer broth) must be at least 24 hours.
2. With the Final Inoculum Suspension (Step 4 in Test System Preparation), inoculate the first surface with 10 µL, at time zero. Begin inoculation about 5 seconds before time zero, and spread aliquot over the surface so it is completed at time zero. Begin the inoculation of the second surface similarly, at given intervals, until all test and control surfaces have been inoculated.
3. At 5 minutes (or other appropriate time) use alcohol-flamed forceps to transfer the surfaces to 30 mL of neutralizer broth in a 50 mL centrifuge tube. Repeat until all test and control surfaces have been completed.
4. Sonicate the samples for 20±2 seconds in a sonicating water bath. Then agitate the samples on an orbital shaker for 3-4 minutes at 250 rpm.

Enumeration of Survivors
1. Serially dilute the control sample suspensions in PBDW and prepare duplicate pour plates of the $10^{-2}$, $10^{-3}$ and $10^{-4}$ dilutions. The control plates must have a minimum of $1\times10^4$ CFU/mL for a valid test.
2. Serially dilute the test sample suspensions in PBDW and prepare duplicate pour plates of the $10^0$, $10^{-2}$ and $10^{-4}$ dilutions.
3. Plate all samples within 30 minutes of their transfer to neutralizer broth.

Method Parameters:

| Raw Materials | Concentration |
|---|---|
| Test composition C - Phase Stable | |
| Vantocil P (HMBG) | 50% |
| Barquat DM50 | 50% |
| Commercial Quaternary Disinfectant | |
| Bardac 208M | 12.5% |
| DI Water | 87.5% |

Test Substance Dilutions:

| Test Substance | Desired Concentration | Diluent | Test Solution (Volume of Test Substance/Total Volume) |
|---|---|---|---|
| Test composition C | 1:64 | 420 ppm Synthetic Hard Water (pH 7.98) | 1.56 mL/100 mL |
| | 1:96 | | 1.04 mL/100 mL |
| | 1:128 | | 0.78 mL/100 mL |
| | 1:256 | | 0.78 mL/200 mL |
| Commercial Quaternary Disinfectant | 1:256 | | 0.78 mL/200 mL |
| | 1:512 | | 0.39 mL/200 mL |

Test Systems: *Staphylococcus aureus* ATCC 6538

*Klebsiella pneumoniae* ATCC 4352

Soil Challenge: 5% Bovine Serum

Test Material: 1"×1" Glass Coverslip

Test Substance Application: 50 µL spread with a pipette tip

Neutralizer Medium: 30 mL Dey Engley Broth

A neutralizer screen was performed as part of the testing, verified that the neutralizer adequately neutralized the product and was not detrimental to the tested organisms.

Plating Medium: Tryptone Glucose Extract Agar

Incubation: 35° C. for 48 hours

| | Inoculum Numbers | | | |
|---|---|---|---|---|
| Test System | Inoculum Suspension | A | B | Average CFU/mL |
| *Staphylococcus aureus* ATCC 6538 | Initial | $112 \times 10^3$ | $145 \times 10^3$ | $1.3 \times 10^5$ |
| | Final | $80 \times 10^6$ | $92 \times 10^6$ | $8.6 \times 10^7$ |
| *Klebsiella pneumoniae* ATCC 4352 | Initial | $77 \times 10^3$ | $87 \times 10^3$ | $8.2 \times 10^4$ |
| | Final | $116 \times 10^6$ | $105 \times 10^6$ | $1.1 \times 10^8$ |

| *Staphylococcus aureus* ATCC 6538 | | | | |
|---|---|---|---|---|
| Test Substance | Survivors (CFU/mL) | Survivors (CFU/Carrier)* | Average CFU/Carrier | Percent Reduction |
| TritonX | $158 \times 10^2, 178 \times 10^2$ $33 \times 10^3, 39 \times 10^3$ | $4.74 \times 10^5, 5.34 \times 10^5$ $9.90 \times 10^5, 1.17 \times 10^6$ | $7.9 \times 10^5$ | N/A |
| Test Composition C (1:64) | $0 \times 10^0, 0 \times 10^0$ $0 \times 10^0, 0 \times 10^0$ | <30, <30, <30, <30 | <30 | >99.996 |
| Test Composition C (1:94) | $3 \times 10^2, 4 \times 10^2$ $10 \times 10^2, 10 \times 10^2$ | $9.00 \times 10^3, 1.20 \times 10^4$ $3.00 \times 10^4, 3.00 \times 10^4$ | $2.0 \times 10^4$ | 97.468 |
| Test Composition C (1:128) | $162 \times 10^0, 158 \times 10^0$ $271 \times 10^0, 255 \times 10^0$ | $4.86 \times 10^3, 4.74 \times 10^3$ $8.13 \times 10^3, 7.65 \times 10^3$ | $6.3 \times 10^3$ | 99.202 |
| Test composition C (1:256) | $101 \times 10^0, 127 \times 10^0$ $137 \times 10^0, 142 \times 10^0$ | $3.03 \times 10^3, 3.81 \times 10^3$ $4.11 \times 10^3, 4.26 \times 10^3$ | $3.8 \times 10^3$ | 99.519 |

*CFU/mL × 30

| *ebsiella pneumoniae* ATCC 4352 | | | | |
|---|---|---|---|---|
| Test Substance | Survivors (CFU/mL) | Survivors (CFU/Carrier)* | Average CFU/Carrier | Percent Reduction |
| TritonX | $176 \times 10^2, 189 \times 10^2$ $145 \times 10^2, 159 \times 10^2$ | $5.28 \times 10^5, 5.67 \times 10^5$ $4.35 \times 10^5, 4.77 \times 10^5$ | $5.0 \times 10^5$ | N/A |
| Test Composition C (1:64) | $0 \times 10^0, 0 \times 10^0$ $5 \times 10^0, 0 \times 10^0$ | <30, <30, <30, <30 $1.50 \times 10^2, 3.00 \times 10^2$ | $<1.3 \times 10^2$ | >99.974 |
| Test Composition C (1:94) | $2 \times 10^2, 3 \times 10^2$ $57 \times 10^0, 53 \times 10^0$ | $6.00 \times 10^3, 9.00 \times 10^3$ $1.71 \times 10^3, 1.59 \times 10^3$ | $4.6 \times 10^3$ | 99.080 |
| Test Composition C (1:128) | $0 \times 10^0, 0 \times 10^0$ $3 \times 10^0, 7 \times 10^0$ | <30, <30 $9.00 \times 10^1, 2.80 \times 10^2$ | $<1.1 \times 10^2$ | >99.987 |
| Test composition C (1:256) | $41 \times 10^0, 35 \times 10^0$ $0 \times 10^0, 0 \times 10^0$ | $1.23 \times 10^3, 1.05 \times 10^3$ <30, <30 | $<5.8 \times 10^2$ | >99.884 |

*CFU/mL × 30

Conclusion:

To be defined as a sanitizer, the test substances on the hard inanimate surface must reduce the total number of organisms by at least 99.9% (based on the Geometric Mean) on the surface within a 5 minute period (after the final inoculation).

Against *S. auerus*, only the 1:64 dilution of test composition C X passed with a greater than 99.9 percent reduction.

Against *K. Pneumoniae*, the 1:64 and 1:128 dilutions of test composition C passed with a greater than 99.9 percent reduction.

Example 7

Residual Hard Surface Test Against PHMB:QAC

Objective:

The objective of the analysis was to examine the residual hard surface efficacy of PHMB:QAC against *Staphylococcus aureus* ATCC 6538 and *Klebsiella pneumoniae* ATCC 4352 after application to inanimate, non-porous, non-food contact surfaces.

Test Method:

Residual Self-Sanitizing Activity on Hard, Non-Porous Surfaces

Test System Preparation

1. At least three consecutive loop transfers of a 24 hour culture of *Staphylococcus aureus* ATCC 6538 and *Klebsiella pneumoniae* ATCC 4352 were performed in 10 mL of AOAC Synthetic broth or AOAC Nutrient broth (respectively) and incubated at 35° C.
2. Final Inoculum Suspension:
   2.1. Vortex an 18-24 hour culture for 3-4 seconds.
   2.2. Add organic soil load to equal 5%, vortex, and let stand for 151 minutes.

Test Surface Preparation

1. Clean glass surfaces by rinsing in alcohol, then sterile water, and allow to air dry.
2. Decontaminate glass surfaces by immersing in absolute ethanol and allowing to air dry (slides can be autoclaved if necessary).
3. Transfer to individual glass petri dishes lined with 1-2 layers of sterile Whatman No. 2 paper, and allow all surfaces to dry completely prior to use (approximately one day).
4. Apply the test substance to the test surfaces on a clean dry surface. Apply test substance to each test surface appropriate to the application instructions. If no application method is specified, apply 50 μL of the test substance to the test surface and spread, with a sterile disposable loop, in an even layer over entire test surface. Allow the surfaces to dry overnight, covered, at room temperature.

5. Apply a 0.01% TritonX 100 solution (made and filter sterilized on the day of application) to each of the control surfaces in the same manner as the test substances. Allow the control surfaces to dry under the same conditions as the test surfaces.

Operating Technique

1. Wear and Reinoculation of Test and Control Surfaces: The treated surfaces will undergo a wear and reinoculation regimen, which will take place over at least a 24 hour period at room temperature.
2. GardCo Washability and Wear Tester: A cycle equals one pass to the left, and a return pass to the right. One pass on the abrasion tester should provide a contact time with the surfaces of approximately 2 seconds.
3. Place one set of surfaces (two test or control surfaces) into the cut out region of the surface wear area on the abrasion tester, and perform 100 cycles of surface wears.
4. Decontaminate the surface wear area with absolute ethanol between each set of surface wears to prevent carry-over contamination. Allow the alcohol to completely evaporate before proceeding. Replace the foam liner and the cotton cloth, on the abrasion boat assembly, between each set of surface wears.
5. The period between test substance application and the initiation of the sanitizer test (carriers into neutralizer broth) must be at least 24 hours.

Enumeration of Survivors

1. With the Final Inoculum Suspension (Step 2 in Test System Preparation), inoculate the first surface with 10 µL, at time zero. Spot inoculate over the entire surface. Begin the inoculation of the second surface similarly, at given intervals, until all test and control surfaces have been inoculated.
2. At 5 minutes (or other appropriate time) use alcohol-flamed forceps to transfer the surfaces to 30 mL of neutralizer broth in a 50 mL centrifuge tube. Repeat until all test and control surfaces have been completed.
3. Vortex the samples on high for one minute.
4. Serially dilute the control sample suspensions in PBDW and prepare duplicate pour plates of the $10^{-2}$, $10^{-3}$ and $10^{-4}$ dilutions. The control plates must have a minimum of $1 \times 10^4$ CFU/mL for a valid test.
5. Serially dilute the test sample suspensions in PBDW and prepare duplicate pour plates of the $10^0$, $10^{-2}$ and 10-4 dilutions. 6. Plate all samples within 30 minutes of their transfer to neutralizer broth.

Method Parameters:
Test Substance Formulas: 1:1 PHMB:QAC
    1:4 PHMB:QAC
    4:1 PHMB:QAC
Ratios based on raw material percentages (e.g. PHMB is 20% and QAC is 50% active) Adjusting for activity testing compositions were
    1:2.5 PHMB:QAC (most preferred)
    1:10 PHMB:QAC (more preferred)
    1:0.625 PHMB:QAC (preferred)
Test Systems: *Staphylococcus aureus* ATCC 6538
    *Klebsiella pneumoniae* ATCC 4352
Soil Challenge: 5% Bovine Serum
Test Material: 1"×1" Glass Surfaces
    1 mm thick non-frosted microscope slides, cut into squares
Test Substance Application: 50 µL spread end to end with a pipette tip
Number of Wears Performed: 12, 24 and 48
Number of Re-inoculations: None
Neutralizer Medium: 30 mL Dey Engley Broth
    A neutralizer screen was performed as part of the testing, verified that the neutralizer adequately neutralized the product and was not detrimental to the tested organisms.
Plating Medium: Tryptone Glucose Extract Agar
Incubation: 35° C. for 48 hours

| | Inoculum Numbers | | | |
|---|---|---|---|---|
| Test System | Inoculum Suspension | A | B | Average CFU/mL |
| *Staphylococcus aureus* ATCC 6538 | Final | $116 \times 10^7$ | $67 \times 10^7$ | $9.2 \times 10^8$ |
| *Klebsiella pneumoniae* ATCC 4352 | Final | $66 \times 10^7$ | $87 \times 10^7$ | $7.6 \times 10^8$ |

| *Staphylococcus aureus* ATCC 6538 | | | | | | |
|---|---|---|---|---|---|---|
| Test Substance | # Wears | CFU/mL | CFU/Carrier* | Average Log Growth | Geometric Mean | Percent Reduction |
| Triton X | NA | $151 \times 10^3$ | $30 \times 10^6$ | 6.64 | $47 \times 10^6$ | NA |
| | | $191 \times 10^3$ | $5.7 \times 10^6$ | | | |
| | NA | $167 \times 10^3$ | $5.0 \times 10^6$ | 6.70 | | |
| | | $171 \times 10^3$ | $5.1 \times 10^6$ | | | |
| 1:1 PHMB:QAC | 12 | $0, 0 \times 10^0$ | $<3.0 \times 10^1$ | 1.48 | $3.0 \times 10^1$ | 99.999 |
| | | $0, 0 \times 10^0$ | $<3.0 \times 10^1$ | 1.48 | | |
| | 24 | $4, 7 \times 10^0$ | $1.6 \times 10^2$ | 2.20 | $6.9 \times 10^1$ | 99.998 |
| | | $0, 0 \times 10^0$ | $<3.0 \times 10^1$ | 1.48 | | |
| | 48 | $258, 262 \times 10^2$ | $7.8 \times 10^5$ | 5.89 | $8.2 \times 10^5$ | 82.553 |
| | | $308, 268 \times 10^2$ | $8.7 \times 10^5$ | 5.94 | | |
| 1:4 PHMB:QAC | 12 | $0, 0 \times 10^0$ | $<3.0 \times 10^1$ | 1.48 | $2.0 \times 10^2$ | 99.996 |
| | | $12, 14 \times 10^0$ | $1.3 \times 10^3$ | 3.11 | | |
| | 24 | $0, 0 \times 10^0$ | $<3.0 \times 10^1$ | 1.48 | $5.0 \times 10^2$ | 99.989 |
| | | $93, 70 \times 10^2$ | $8.2 \times 10^3$ | 3.91 | | |
| | 48 | $430, 442 \times 10^2$ | $1.3 \times 10^6$ | 6.11 | $1.5 \times 10^6$ | 68.085 |
| | | $508, 620 \times 10^2$ | $1.7 \times 10^6$ | 6.23 | | |
| 4:1 PHMB:QAC | 12 | $7, 7 \times 10^0$ | $2.1 \times 102$ | 2.32 | $7.9 \times 10^1$ | 99.998 |
| | | $0, 0 \times 10^0$ | $<3.0 \times 101$ | 1.48 | | |
| | 24 | $596, 572 \times 10^0$ | $1.7 \times 10^4$ | 4.23 | $1.5 \times 10^4$ | 99.681 |
| | | $504, 420 \times 10^0$ | $1.4 \times 10^4$ | 4.15 | | |

| | | Staphylococcus aureus ATCC 6538 | | | | |
|---|---|---|---|---|---|---|
| Test Substance | # Wears | CFU/mL | CFU/Carrier* | Average Log Growth | Geometric Mean | Percent Reduction |
| | 48 | 53, 52 × 10² 16, 20 × 10² | 1.6 × 10⁵ 5.4 × 10⁴ | 5.20 4.73 | 9.2 × 10⁴ | 98.042 |

*Average CFU/mL × Total Volume of Neutralized Test Substance (30 L).

Conclusion:
To be defined as a sanitizer, the test substances on the hard inanimate surface must reduce the total number of organisms by at least 99.9% (based on the Geometric Mean) on the surface within a 5 minute period (after the final inoculation).

The 4:1 ratio of PHMB:QAC had the best durability over time with 98% reduction of 48 wears.

Example 8

Residual Hard Surface Test Against PHMB and QAC Alone

Objective:
The objective of the analysis was to examine the residual hard surface efficacy of QAC, PHMB and a conventional commercial disinfectant (Disinfectant B) vs. the Test Composition A (PHMB:QAC blend) against *Staphylococcus aureus* ATCC 6538 after application to inanimate, non-porous, non-food contact surfaces.

Test Method:
Residual Self-Sanitizing Activity on Hard, Non-Porous Surfaces

Test System Preparation
1. At least three consecutive loop transfers of a 24 hour culture of *Staphylococcus aureus* ATCC 6538 and *Klebsiella pneumoniae* ATCC 4352 were performed in 10 mL of AOAC Synthetic broth or AOAC Nutrient broth (respectively) and incubated at 35° C.
2. Final Inoculum Suspension:
   2.1. Vortex an 18-24 hour culture for 3-4 seconds.
   2.2. Make one 1/10 dilution in sterile PBDW and vortex.
   2.3. Add organic soil load to equal 5% vortex, and let stand for 151 minutes.

Test Surface Preparation
1. Clean glass surfaces by rinsing in alcohol, then sterile water, and allow to air dry.
2. Decontaminate glass surfaces by immersing in absolute ethanol. Transfer to individual glass petri dishes lined with 1-2 layers of sterile Whatman No. 2 paper, and allow all surfaces to dry completely prior to use (approximately one day). Slides can be autoclaved if desired.
3. Apply the test substance to the test surfaces on a clean dry surface. Apply test substance to each test surface appropriate to the application instructions. If no application method is specified, apply 50 µL of the test substance to the test surface and spread, with a sterile disposable loop, in an even layer over entire test surface. Allow the surfaces to dry overnight, covered, at room temperature.
5. Apply a 0.01% TritonX 100 solution (made and filter sterilized on the day of application) to each of the control surfaces in the same manner as the test substances. Allow the control surfaces to dry under the same conditions as the test surfaces.

Operating Technique
1. Wear and Reinoculation of Test and Control Surfaces: The treated surfaces will undergo a wear and reinoculation regimen, which will take place over at least a 24 hour period at room temperature.
2. GardCo Washability and Wear Tester: A cycle equals one pass to the left, and a return pass to the right. One pass on the abrasion tester should provide a contact time with the surfaces of approximately 2 seconds.
3. Place one set of surfaces (two test or control surfaces) into the cut out region of the surface wear area on the abrasion tester, and perform 100 cycles of surface wears.
4. The period between test substance application and the initiation of the sanitizer test (carriers into neutralizer broth) must be at least 24 hours.

Enumeration of Survivors
1. With the Final Inoculum Suspension (Step 2 in Test System Preparation), inoculate the first surface with 10 µL, at time zero. Begin inoculation about 5 seconds before time zero. Spot the aliquot over the surface so it is completed at time zero. Begin the inoculation of the second surface similarly, at given intervals, until all test and control surfaces have been inoculated.
2. At 10 minutes use alcohol-flamed forceps to transfer the surfaces to 20 mL of neutralizer broth in a sterile straight-sided jar. Repeat until all test and control surfaces have been completed.
3. Sonicate the samples for 20±2 seconds in a sonicating water bath. Then agitate the samples on an orbital shaker for 4 minutes at 250 rpm.
4. Serially dilute the control sample suspensions in PBDW and prepare duplicate pour plates of the $10^{-2}$, $10^{-3}$ and $10^{-4}$ dilutions. The control plates must have a minimum of $1×10^4$ CFU/mL for a valid test.
5. Serially dilute the test sample suspensions in PBDW and prepare duplicate pour plates of the $10^0$, $10^{-2}$ and 10-4 dilutions.
6. Plate all samples within 30 minutes of their transfer to neutralizer broth.
7. Incubate all plates and tubes at 35±2° C. for 484 hours.

Method Parameters:
Test Substances: Quaternary disinfectant B—
   Benzyl Quat (Bardac DM50)
   PHMB (Vantocil P)

| Test Substance | Test concentration | Diluent |
|---|---|---|
| Disinfectant B | Diluted to 3900 ppm active QAC 625 ppm active PHMB | Sterile MilliQ Water |
| Bardac DM 50 | Diluted to 3900 ppm QAC | |
| Vantocil P | Diluted to 625 ppm PHMB | |

Test Systems: *Staphylococcus aureus* ATCC 6538
Soil Challenge: 5% Bovine Serum
Test Material: 1"×1" Glass Surfaces 1 mm thick non-frosted microscope slides, cut into squares
Test Substance Application: 50 μL applied and spread end to end with a pipette tip
Number of Wears Performed: 10, 20, 30 and 40
Neutralizer Medium: 20 mL Dey Engley Broth
  A neutralizer screen was performed as part of the testing, verified that the neutralizer adequately neutralized the product and was not detrimental to the tested organisms.
Plating Medium: Tryptone Glucose Extract Agar
Incubation: 35° C. for 48 hours
Results:
Test Date: May 12, 2010
Date Results Read: May 14, 2010

| | Inoculum Numbers | | |
|---|---|---|---|
| Test System | A | B | Average CFU/mL |
| *Staphylococcus aureus* ATCC 6538 | $115 \times 10^7$ | $111 \times 10^7$ | $1.13 \times 10^9$ |

Bardac 205M is a commercially available blended linear alkyl quaternary ammonium chloride blend from Lonza Group Ltd, Muenchensteinerstrasse 38, CH-4002 Basel, Switzerland.

FMB AO-8 is a commercially available Octyl di-methyl amine oxide (40% active as concentrate) from Lonza Group Ltd, Muenchensteinerstrasse 38, CH-4002 Basel, Switzerland.

Versene 100 is a commercially available 40% solution of tetra sodium ethylene diamine tetra acetic acid from The Dow Chemical Company Midland, Mich. 48674 U.S.A.

Trilon M is a commercially available trisodium salt of methylglycinediacetic acid (Na3MGDA) available from BASF Corporation, 100 Campus Drive, Florham Park, N.J. 07932.

Lutensol TDA-9 is a commercially available 9 mole ethoxylate of tridecyl alcohol from BASF Corporation, 100 Campus Drive, Florham Park, N.J. 07932.

Vantocil P is a commercially available 20% solution of poly hexamethylene biguanide Arch Chemicals, Inc. 5660 New Northside Drive, Suite 1100 Atlanta, Ga. 30328.

A test sample concentrate was prepared according to the invention per below:

*Staphylococcus aureus* ATCC 6538

| Test Substance | Wears | Rep | CFU/Carrier | $\text{Log}_{10}$ Growth | Geometric Mean* | Percent Reduction |
|---|---|---|---|---|---|---|
| Triton X | 10 | 1 | $9.00 \times 10^6$ | 6.95 | $9.00 \times 10^6$ | N/A |
| | | 2 | $7.00 \times 10^6$ | 6.84 | | |
| | 20 | 1 | $5.00 \times 10^6$ | 6.70 | $9.00 \times 10^6$ | N/A |
| | | 2 | $6.20 \times 10^6$ | 6.79 | | |
| | 30 | 1 | $5.80 \times 10^6$ | 6.76 | $9.00 \times 10^6$ | N/A |
| | | 2 | $1.60 \times 10^6$ | 6.20 | | |
| | 40 | 1 | $2.00 \times 10^6$ | 6.30 | $9.00 \times 10^6$ | N/A |
| | | 2 | $7.80 \times 10^6$ | 6.89 | | |
| Quaternary Disinfectant B | 10 | 1 | $2.00 \times 10^1$ | 1.30 | $9.00 \times 10^6$ | 99.952% |
| | | 2 | $7.36 \times 10^5$ | 5.87 | | |
| | 20 | 1 | $7.52 \times 10^5$ | 5.88 | $9.00 \times 10^6$ | 99.930% |
| | | 2 | $<2.00 \times 10^1$ | <1.30 | | |
| | 30 | 1 | $1.60 \times 10^6$ | 6.20 | $9.00 \times 10^6$ | 95.087% |
| | | 2 | $1.40 \times 10^4$ | 4.15 | | |
| | 40 | 1 | $2.00 \times 10^6$ | 6.30 | $9.00 \times 10^6$ | 57.634% |
| | | 2 | $1.40 \times 10^6$ | 6.15 | | |
| Bardac DM50 | 10 | 1 | $1.60 \times 10^6$ | 6.20 | $9.00 \times 10^6$ | 91.689% |
| | | 2 | $2.72 \times 10^5$ | 5.43 | | |
| | 20 | 1 | $1.36 \times 10^5$ | 5.13 | $9.00 \times 10^6$ | 95.354% |
| | | 2 | $4.92 \times 10^5$ | 5.69 | | |
| | 30 | 1 | $1.96 \times 10^5$ | 5.29 | $9.00 \times 10^6$ | 99.935% |
| | | 2 | $<2.00 \times 10^1$ | <1.30 | | |
| | 40 | 1 | $4.00 \times 10^3$ | 3.60 | $9.00 \times 10^6$ | 98.399% |
| | | 2 | $1.00 \times 10^6$ | 6.00 | | |
| Vantocil P | 10 | 1 | $3.80 \times 10^6$ | 6.58 | $9.00 \times 10^6$ | 56.066% |
| | | 2 | $3.20 \times 10^6$ | 6.50 | | |
| | 20 | 1 | $2.20 \times 10^6$ | 6.34 | $9.00 \times 10^6$ | 68.479% |
| | | 2 | $1.40 \times 10^6$ | 6.15 | | |
| | 30 | 1 | $1.80 \times 10^6$ | 6.26 | $9.00 \times 10^6$ | 5.541% |
| | | 2 | $4.60 \times 10^6$ | 6.66 | | |
| | 40 | 1 | $4.00 \times 10^6$ | 6.60 | $9.00 \times 10^6$ | 0.000% |
| | | 2 | $5.20 \times 10^6$ | 6.72 | | |

* = Antilog $[(\log_1 + \log_2)/2]$

Example 9

Bardac MB 50 is a commercially available alkyl dimethyl benzyl quaternary ammonium chloride from Lonza Group Ltd, Muenchensteinerstrasse 38, CH-4002 Basel, Switzerland.

| TS1 |
|---|
| 50% Bardac 205M |
| 20% Vantocil P |
| 30% Distilled water |

| TS2 |
|---|
| 50% Bardac 205M |
| 20% Vantocil P |
| 6% Lutensol TDA-9 |
| 8% Trilon M |
| 16% Water |

The formulation (TS1) was then tested for bactericidal activity against *Pseudomonas aeruginosa* using the OECD Quantitative Method for Evaluating Bacteriocidal activity of Microbiocides used on hard, non-porous surfaces
Microorganism Preparation

*Pseudomonas aeruginosa* ATCC 15442, was propagated and prepared according to the OECD bacteriocidal method. (Centrifuged 10,000 g for 20 minutes and resuspended in 1 mL PBS). Soil Load: 25 µL BSA, 100 µl mucin, 35 µL yeast extract.

Carriers: Magnetized stainless steel disks (1 cm in diameter, 0.7 mm thick)—washed in a 5% DECON-Clean solution, rinsed in deionized water, dried and autoclaved.

Carrier Inoculation: 10 µL of the soil/bacteria mixture was placed in the center of each carrier. The carriers were dried under vacuum at ambient temperature for 1 hour.
Test Substances:
The test substance (TS1) was serially diluted in OECD hard water and labeled #1-#8.

| Sample ID | Composition |
|---|---|
| A | TS1 @ 8 oz./gal. |
| B | TS1 @ 4 oz./gal. |
| C | TS1 @ 1.0 oz./gal |
| D | TS1 @ 0.75 oz./gal |
| E | TS1 @ 0.5 oz./gal |
| F | TS1 @ 0.25 oz./gal |
| G | TS1 @ 1.0 oz./gal plus Lutensol TDA-9 and Trilon M at equal level as in example 8 |
| H | TS2 @ 8.0 oz/gal |

Test Temperature: Ambient (15-30° C.)
Exposure Time: 5 minutes
Neutralizer: 10 mL of DeyEngly Broth (DE)
Media: Tryptic Soy Agar
Incubation 35±2° C. for 2 days General Test Procedure:

Dried, inoculated carriers were placed inside of small plastic medicine jars. 50 µL of diluted test substances was placed on the center of each disk at intervals of 15 seconds.

After the specified exposure time (ambient exposure temperature), each disk was neutralized at the appropriate interval. Each vial was then vortexed for 30 seconds. 1.0 mL from the medicine jar ($10^{-1}$) and 1.0 mL of a 1:100 dilution in Phosphate Buffered Dilution Water ($10^{-3}$) were pour plated, and the remaining was added to a pre-wet (with saline) analytical filter unit. The medicine jar was washed with 20 mL of saline tree times, with each washing added to the filter unit. A magnet was placed on the outside of the jar to hold the carrier in the jar while pouring out the liquid. The liquid was filtered through the membrane via a vacuum connection, and the funnels were rinsed with 40 mL of saline and then filtered through the membrane. The membranes were aseptically added to the appropriate agar medium. Three carriers were used for each test condition.

For the carrier enumeration controls, four carriers were used per time point. 50 µL of saline was added to each carrier. After the desired exposure time, 10 mL of the neutralizer was added to each carrier (in the same medicine jars as above). The carrier enumeration controls were pour plated. The $10^{-2}$, $10^{-3}$ and $10^{-4}$ dilutions were plated.

| | Number Centrals | | | | |
|---|---|---|---|---|---|
| Test System | C1 | C2 | C3 | C4 | Ave |
| *P. aeruginosa* | $553 \times 10^4$ | $458 \times 10^4$ | $602 \times 10^4$ | $550 \times 10^4$ | $5.4 \times 10^6$ |

| Culture #s | |
|---|---|
| Test System | CFU/mL |
| *P. aeruginosa* | $351 \times 10^7$ |
| | $3.5 \times 10^9$ |

| *Pseudomonas Aeruginosa* | | | | | | |
|---|---|---|---|---|---|---|
| Sample | Replicate | CFU/Carrier | Ave CFU/Carrier | Log | Log Reduction | % Reduction |
| TS1 @ 8 oz./gal. | 1 | $72 \times 10^1$ | $2.8 \times 10^2$ | 2.44 | 4.29 | 99.994 |
| | 2 | 30 | | | | |
| | 3 | 79 | | | | |
| TS1 @ 4 oz./gal. | 1 | 43 | $23 \times 10^2$ | 1.36 | 5.37 | 99.999 |
| | 2 | 18 | | | | |
| | 3 | 7 | | | | |
| TS1 @ 1.0 oz./gal | 1 | $36 \times 10^3$ | $3.1 \times 10^4$ | 4.49 | 2.24 | 99.42 |
| | 2 | $34 \times 10^3$ | | | | |
| | 3 | $23 \times 10^3$ | | | | |
| TS1 @ 0.75 oz./gal | 1 | $94 \times 10^3$ | $4.5 \times 10^4$ | 4.65 | 2.08 | 99.16 |
| | 2 | $244 \times 10^1$ | | | | |
| | 3 | $40 \times 10^3$ | | | | |
| TS1 @ 0.5 oz./gal | 1 | $183 \times 10^3$ | $2.6 \times 10^5$ | 5.41 | 1.32 | 95.18 |
| | 2 | $826 \times 10^3$ | | | | |
| | 3 | $357 \times 10^3$ | | | | |
| TS1 @ 0.25 oz./gal | 1 | $567 \times 10^3$ | $>8.6 \times 10^5$ | >5.93 | <0.80 | No reduction |
| | 2 | $>1000 \times 10^3$ | | | | <84.07% |
| | 3 | $>1000 \times 10^3$ | | | | |
| TS1 @ 1.0 oz./gal plus | 1 | $90 \times 10^3$ | $<3.0 \times 10^2$ | <2.47 | >4.26 | >99.994 |
| | 2 | 0 | | | | |
| | 3 | 0 | | | | |

-continued

| | | | Pseudomonas Aeruginosa | | | |
|---|---|---|---|---|---|---|
| Sample | Replicate | CFU/Carrier | Ave CFU/Carrier | Log | Log Reduction | % Reduction |
| Amine Oxide and EDTA at equal level as in example 8 TS2 @ 8.0 oz/gal.. | 1 | 0 | <1 | 0 | >6.73 | >99.99998 |
| | 2 | 0 | | | | |
| | 3 | 0 | | | | |

As can be seen, the addition of surfactant and chelant gave superior reduction in the presence of *Pseudomonas Aeruginosa* over the compositions comprising the quaternary ammonium compound and cationic biocide alone.

Additional Formulations were Made and Tested as Per Below:

The data outlined in the next 2 tables is outlined in examples #9-#13. Unless we see a reason to break those out as a composite I would recommend that we delete these 2 tables and level the data as disparate within the examples. When it comes to examination of the application I have specified in the examples the critical comparisons referenced to test ID numbers and example numbers so the support data can be easily found.

| | Quat (ppm) | PHMB (ppm) | TDA (ppm) | AO-8 | Trilon M (Active Ppm) | Versene 100 | | | OECD LR | Physical | | | | |
|---|---|---|---|---|---|---|---|---|---|---|---|---|---|---|
| 1 | 1953 | 312.5 | 0 | | 0 | | 3.25 | 99.94 | Clear | | | | | |
| 2 | 1953 | 312.5 | 500 | | 500 | | 2.8 | 99.84 | Clear | | | | | |
| 3 | 1953 | 312.5 | 500 | | 2000 | | >6.69 | >99.9999 | Very cloudy | | | | | |
| 4 | 1953 | 312.5 | 1000 | | 1000 | | >5.79 | >99.999 | Slight cloudy | | | | | |
| 5 | 1953 | 312.5 | 2000 | | 500 | | 2.65 | 99.7 | Clear | | | | | |
| 6 | 1953 | 312.5 | 2000 | | 2000 | | >6.69 | >99.9999 | Very cloudy | | | | | |
| 7 | 1953 | 312.5 | 2000 | | 0 | | 2.26 | 99.46 | Clear | | | | | |
| 8 | 1953 | 312.5 | 0 | | 2000 | | 4.44 | 99.99 | Very cloudy | | | | | |
| 9 | 1953 | 312.5 | 0 | | 0 | | 2.54 | 99.7 | Clear | | | | | |
| 10 | 1953 | 312.5 | 500 | | 1000 | | >5.77 | >99.999 | Clear | | | | | |
| 11 | 1953 | 312.5 | 500 | | 500 | | 3.14 | 99.9 | Clear | pH 11 | | | | |
| 12 | 1953 | 312.5 | 500 | | | 500 | 3.6 | 99.94 | Clear | EDTA vs trilon | | | | |
| 13 | 1953 | 312.5 | 500 | | 2000 | | >6.07 | >99.9999 | Clear | pH 8.5 | | | | |
| 14 | 3905 | 625 | 500 | | 500 | | >6.07 | >99.9999 | Clear | 2 oz/gal actives | | | | |
| 15 | 1953 | 312.5 | 0 | 500 | 500 | | >5.47 | >99.9992 | Clear | Barlox vs. TDA | | | | |
| 16 | 1953 | 312.5 | 500 | | 500 | | 4.3 | 99.99 | Clear | MB50 vs. 205M | | | | |
| | | | | | | | | | | | 0 | 0 | 0 | 0 |
| 17 | 977 | 312.5 | 0 | 0 | 0 | | 1.6 | 97.45 | Clear | MB50 | 1.954 | 1.954 | 2.579 | 2.579 |
| 18 | 977 | 312.5 | 0 | 500 | 500 | | 2.3 | 99.5 | Clear | MB50 | 0 | 0 | 0 | 0 |
| 19 | 1953 | 312.5 | 0 | 0 | 0 | | 2.34 | 99.5 | Clear | 2 oz/gal actives | 0.977 | 1.954 | 1.2895 | 2.579 |
| 20 | 977 | 312.5 | 0 | 500 | 1000 | | 2.48 | 99.6 | Clear | MB50 with PG water | 0.977 | 0.4885 | 1.2895 | 0.64475 |
| 21 | 977 | 312.5 | 0 | 2000 | 1000 | | 3.73 | 99.98 | Clear | MB50 | 0.977 | 3.908 | 1.2895 | 5.158 |
| 22 | 977 | 312.5 | 0 | 250 | 1000 | | 3.79 | 99.98 | Clear | MB50 | 0.977 | 1.954 | 1.2895 | 2.579 |
| 23 | 977 | 312.5 | 0 | 500 | 1000 | | 3.85 | 99.98 | Clear | MB50 | 0.977 | 0.977 | 1.2895 | 1.2895 |
| 24 | 977 | 312.5 | 0 | 1000 | 1000 | | 4.81 | 99.998 | Clear | MB50 | | | | |

Summary of the Results of the Foregoing Table are Shown Below:

| Composition | MB50 | 205M | PHMB | TDA-9 | AO-8 | Trilon | Versene | Physical | pH | Log reduction |
|---|---|---|---|---|---|---|---|---|---|---|
| Turbid vs. non turbid examples | | | | | | | | | | |
| 10 | 25 | | 10 | 3.2 | | 16 | | Clear | 10 | >5.77 |
| 4 | 25 | | 10 | 6.4 | | 16 | | Slight cloudy | 10 | >5.79 |
| 13 | 25 | | 10 | 3.2 | | 32 | | Clear | 8.5 | >6.07 |
| 3 | 25 | | 10 | 3.2 | | 32 | | Very cloudy | 10 | >6.69 |
| 205m vs. MB50 | | | | | | | | | | |
| 11 | 25 | | 10 | 3.2 | | 8 | | Clear | 11 | 3.14 |
| 16 | | 25 | 10 | 3.2 | | 8 | | Clear | 10 | 4.3 |
| EDTA vs. Triton | | | | | | | | | | |
| 2 | 25 | | 10 | 3.2 | | 8 | | Clear | 10 | 2.8 |
| 12 | 25 | | 10 | 3.2 | | | 8 | Clear | 10 | 3.6 |
| Ratio chelant to TDA or QAC | | | | | | | | | | |
| 2 | 25 | | 10 | 3.2 | | | | Clear | 10 | 2.8 |
| 12 | 25 | | 10 | 3.2 | | 8 | | Clear | 10 | 3.6 |
| 10 | 25 | | 10 | 3.2 | | | 8 | Clear | 10 | >5.77 |
| 13 | 25 | | 10 | 3.2 | | 16 32 | | Clear | 8.5 | >6.07 |
| TDA vs. AO-8 | | | | | | | | | | |
| 15 | 25 | | 10 | 3.2 | 8 | 8 | | Clear | 10 | >5.47 |
| 2 | 25 | | 10 | 3.2 | | 8 | | Clear | 10 | 2.8 |

As can be seen, the use of amine oxide compared to TDA gave far superior and more than two logs better reduction in bacteria. Also, the comparison of ration of chelant to TDA or QAC showed that increasing the ratio of chelant to quat by as much as 2 to 3 times greatly improved reduction on bacteria.

Example 10

The concentration gradient experiment from example 9 demonstrated the ability to achieve a high level of microbial efficacy in "wet" applications. However, the levels of chemistry required to achieve the required levels of efficacy (minimum 3 logs) were at concentrations (TS1 @ 4-8 oz/gallon) that were likely to cause problems from a cost and eye irritancy perspective.

As such we undertook a series of designed experiments to optimize the concentration of biocidal actives, their preferred embodiment and the critical concentrations of adjuncts required to achieve a high level of bactericidal efficacy against gram negative organisms (e.g. *Pseudomonas aeruginosa*)

Experimentally we composed a series of compositions inclusive of different levels of chelant and surfactants to determine an optimum.

These solutions were diluted @ a ratio of 1 oz/gallon of water to produce the active solutions for microbial testing. The compositions in this experiment when diluted to 1 oz/gal level contained QAC ~1950 ppm and PHMB ~310 ppm.

| Raw materials by weight (g) | | | | | |
|---|---|---|---|---|---|
| Sample ID | QAC | PHMB | TDA | Trilon M | Water |
| 1 | 12.50 | 5.00 | 0.00 | 0.00 | 32.50 |
| 2 | 12.50 | 5.00 | 1.60 | 4.00 | 26.90 |
| 3 | 12.50 | 5.00 | 1.60 | 16.00 | 14.90 |
| 4 | 12.50 | 5.00 | 3.20 | 8.00 | 21.30 |
| 5 | 12.50 | 5.00 | 6.40 | 4.00 | 22.10 |
| 6 | 12.50 | 5.00 | 6.40 | 16.00 | 10.10 |
| 7 | 12.50 | 5.00 | 6.40 | 0.00 | 26.10 |
| 8 | 12.50 | 5.00 | 0.00 | 16.00 | 16.50 |

| Critical ranges of surfactant and chelant | | |
|---|---|---|
| Sample | TDA | Trilon M |
| 1 | 0 | 0 |
| 2 | 500 | 500 |
| 3 | 500 | 2000 |
| 4 | 1000 | 1000 |
| 5 | 2000 | 500 |
| 6 | 2000 | 2000 |
| 7 | 2000 | 0 |
| 8 | 0 | 2000 |

Concentrate samples 3, 6, 8 separated upon sitting. All samples were shaken before dilution to ensure uniformity. Microbiological Test Method: Quantitative Method for evaluations bactericidal activity of microbiocides used on hard, non-porous surfaces (OECD) Rev. Mar. 10, 2010.

Test Systems: *Pseudomonas aeruginosa* ATCC 15442
Propagated and prepared according to the OECD bacteriocidal method. (Centrifuged 1000 g for 20 minutes and resuspended in 1 mL PBS).

Soil Load: 25 µL BSA, 100 µL mucin, 35 µL yeast extract.
Carriers: Magnetized stainless steel disks (1 cm in diameter, 0.7 mm thick)—washed in a 5% DECON-Clean solution, rinsed in deionized water, dried and autoclaved.

Carrier Inoculation: 10 μL of the soil/bacteria mixture was placed in the center of each carrier. The carriers were dried under vacuum at ambient temperature for 1 hour.

Test Substances:
Test Temperature: Ambient (15-30° C.)
Exposure Time: 5 minutes

For the carrier enumeration controls, four carriers were used per time point. 50 μL of saline was added to each carrier. After the desired exposure time, 10 mL of the neutralizer was added to each carrier (in the same medicine jars as above). The carrier enumeration controls were pour plated. The $10^{-2}$, $10^{-3}$ and $10^{-4}$ dilutions were plated.

| Culture #s | | |
|---|---|---|
| Test System | CFU/mL | Ave CFU/mL |
| *P. aeruginosa* | 237, 235 × $10^7$ | 2.36 × $10^9$ |

| Number Controls | | | | | |
|---|---|---|---|---|---|
| Test System | C1 | C2 | C3 | C4 | Ave CFU/mL |
| *P. aeruginosa* | 500 × $10^4$ | 357 × $10^4$ | 606 × $10^4$ | 521 × $10^4$ | 5.0 × $10^6$ |

| | | | | | Log 6.69 | |
|---|---|---|---|---|---|---|
| Sample | Replicate | CFU/Carrier | Ave CFU/Carrier | Log | Log Reduction | % Reduction |
| 1 | 1 | 70 × $10^1$ | 2.8 × $10^3$ | 3.44 | 3.25 | 99.9 |
|   | 2 | 232 × $10^1$ | | | | |
|   | 3 | 524 × $10^1$ | | | | |
| 2 | 1 | 232 × $10^1$ | 7.8 × $10^3$ | 3.89 | 2.80 | 99.8 |
|   | 2 | 24 (0) | | | | |
|   | 3 | 21 × $10^3$ | | | | |
| 3 | 1 | 0 (0) | <1 | 0 | >6.69 | >99.9999 |
|   | 2 | 0 (0) | | | | |
|   | 3 | 0 (0) | | | | |
| 4 | 1 | 0 (0) | <8 | <0.90 | >5.79 | >99.999 |
|   | 2 | 0 (0) | | | | |
|   | 3 | 22 (0) | | | | |
| 5 | 1 | 34 × $10^3$ | 1.1 × $10^4$ | 4.04 | 2.65 | 99.7 |
|   | 2 | 7 (0) | | | | |
|   | 3 | 15 (0) | | | | |
| 6 | 1 | 0 (0) | <1 | 0 | >6.69 | >99.9999 |
|   | 2 | 0 (0) | | | | |
|   | 3 | 0 (0) | | | | |
| 7 | 1 | 43 × $10^3$ | 2.7 × $10^4$ | 4.43 | 2.26 | 99.4 |
|   | 2 | 33 × $10^3$ | | | | |
|   | 3 | 7 × $10^3$ | | | | |
| 8 | 1 | 334 × $10^1$ 55 × $10^1$ | 1.8 × $10^2$ | 2.25 | 4.44 | 99.99 |
|   | 2 | 0 (0) | | | | |
|   | 3 | 0 (0) | | | | |

Neutralizer: 10 mL of DeyEngly Broth (DE)
Media: Tryptic soy Agar
Incubation: 35±2° C. for 2 days
General Test Procedure:

Dried, inoculated carriers were placed inside of small plastic medicine jars. 50 μL of diluted test substance was placed onto the center of each disk at intervals of 15 seconds. After the specified exposure time (ambient exposure temperature), each disk was neutralized at the appropriate interval. Each vial was then vortexed for 30 seconds.

1.0 mL from the medicine jar ($10^{-1}$) and 1.0 mL of a 1:100 dilution in Phosphate buffered Dilution Water ($10^{-3}$) were pour plated, and the remaining was added to a pre-wet (with saline) analytical filter unit. The medicine jar was washed with 20 mL of saline three times, with each washing added to the filter unit. A magnet was placed on the outside of the jar to hold the carrier in the jar while pouring out the liquid. The liquid was filtered through the membrane via a vacuum connection, and the funnels were rinsed with 40 mL of saline and then filtered through the membrane. The membranes were aseptically added to the appropriate agar medium. Three carriers were used for each test condition.

This $1^{st}$ DOE highlights the importance of inclusion of chelant in the composition for enhancement of wet efficacy of the blend of PHMB and QAC (see #1 vs. #8)

It also highlights the detrimental effect of nonionic surfactant in this composition in the absence of chelant (see #1 vs. #7) and importance of chelant concentration relative to PHMB and QAC (see #2, 3, 4 and 5)

Example 11

This example entails an expansion of the OCED design outlined in example #10. It included focus on pH of the concentrates, impact of phase stability of the concentrates, choice of chelant for optimum efficacy, selection of benzyle quat vs. a linear quat (Lonza MB50 vs. Lonza 205M) and evaluation of an amine oxide as an alternative to the linear non-ionic surfactant TDA-9.

| Sample | Bardac 205M | PHMB | TDA | Trilon M | Water | Barlox AO-8 | Barquat MB50 | EDTA |
|---|---|---|---|---|---|---|---|---|
| 9 | 12.50 | 5.00 | 0.00 | 0.00 | 32.50 | | | |
| 10 | 12.50 | 5.00 | 1.60 | 8.00 | 22.90 | | | |
| 11 | 12.50 | 5.00 | 1.60 | 4.00 | 26.90 | | pH 11.0 | |
| 12 | 12.50 | 5.00 | 1.60 | | 26.90 | | | 4.00 |
| 13 | 12.50 | 5.00 | 1.60 | 16.00 | 14.90 | | | |
| 14 | 25.00 | 10.00 | 1.60 | 4.00 | 9.40 | | | |
| 15 | 12.50 | 5.00 | | 4.00 | 24.50 | 4.00 | | |
| 16 | | 5.00 | 1.60 | 4.00 | 26.90 | | 12.50 | |

Sample 11 adjusted to pH 11 with NaOH.
Sample 13 adjusted to pH 8.5 with Phos Acid.

Each of these compositions was diluted 1 oz/gallon with OECD hard water and evaluated for microbial efficacy against *Pseudomonas aeruginosa* using the Quantitative Method for evaluations bactericidal activity of microbiocides used on hard, non-porous surfaces (OECD) as outlined previously.

| | Culture #s | |
|---|---|---|
| Test System | | CFU/mL |
| *P. aeruginosa* | | $34 \times 10^7$ |

| | | Number Controls | | | |
|---|---|---|---|---|---|
| Test System | C1 | C2 | C3 | C4 | Ave CFU/mL |
| *P. aeruginosa* | $126 \times 10^4$ | $117 \times 10^4$ | $154 \times 10^4$ | $88 \times 10^4$ | $1.2 \times 10^6$ |

| | | | | | Log 6.07 | |
|---|---|---|---|---|---|---|
| Sample | Replicate | CFU/Carrier | Ave CFU/Carrier | Log | Log Reduction | % Reduction |
| 9 | 1 | $292 \times 10^1$ | $3.4 \times 10^3$ | 3.53 | 2.54 | 99.7 |
| | 2 | $226 \times 10^1$ | | | | |
| | 3 | $5 \times 10^3$ | | | | |
| 10 | 1 | 0 | <2 | <0.30 | >5.77 | >99.999 |
| | 2 | 0 | | | | |
| | 3 | 3 | | | | |
| 11 | 1 | $242 \times 10^1$ | $8.6 \times 10^2$ | 2.93 | 3.14 | 99.9 |
| | 2 | 13 | | | | |
| | 3 | $12 \times 10^{-1}$ 164(0) | | | | |
| 12 | 1 | $74 \times 10^1$ | $3.0 \times 10^2$ | 2.47 | 3.60 | 99.9 |
| | 2 | 4 | | | | |
| | 3 | $19 \times 10^1$ 100(0) | | | | |
| 13 | 1 | 1 | <1 | 0 | >6.07 | >99.9999 |
| | 2 | 0 | | | | |
| | 3 | 0 | | | | |
| 14 | 1 | 0 | <1 | 0 | >6.07 | >99.9999 |
| | 2 | 0 | | | | |
| | 3 | 0 | | | | |
| 15 | 1 | 2 | <4 | <0.60 | >5.47 | >99.999 |
| | 2 | 8 | | | | |
| | 3 | 0 | | | | |
| 16 | 1 | $9 \times 10^1$ 53(0) | $6.0 \times 10^1$ | 1.77 | 4.30 | 99.99 |
| | 2 | 80 | | | | |
| | 3 | 28 | | | | |

The results from these experiments highlight a range of critical discoveries. The clear advantage of amine oxide vs. an alcohol ethoxylate surfactant for enhanced efficacy (see #11 vs #15). The ability to markedly reduce the level of QAC and PHMB required to achieve a high level of efficacy with optimized concentrations of chelant and surfactant selection (See #14 vs. #15) and to confirm the critical ratio of chelant to biocide (see #9, 10 and 11)

Example 12

This third set of designed experiments focused on optimization of the ratios of critical ingredients identified in Examples #10 and #11. It has a focus on the critical level of amine oxide as well as the chelant.

| | Ideal (g) | | | | | |
|---|---|---|---|---|---|---|
| Sample | QAC | PHMB | FMB-AO8 | EDTA | PG Ester | Water |
| 17 | 6.25 | 5.00 | 0.00 | 0.00 | 0.00 | 38.75 |
| 18 | 6.25 | 5.00 | 2.00 | 8.00 | 0.00 | 28.75 |
| 19 | 6.25 | 5.00 | 4.00 | 8.00 | 0.00 | 26.75 |
| 20 | 6.25 | 5.00 | 8.00 | 8.00 | 0.00 | 22.75 |
| 21 | 6.25 | 5.00 | 16.00 | 8.00 | 0.00 | 14.75 |
| 22 | 12.50 | 5.00 | 0.00 | 0.00 | 0.00 | 32.50 |

-continued

| | Ideal (g) | | | | | |
|---|---|---|---|---|---|---|
| Sample | QAC | PHMB | FMB-AO8 | EDTA | PG Ester | Water |
| 23 | 6.25 | 5.00 | 4.00 | 8.00 | 3.20 | 23.55 |
| 24 | 6.25 | 5.00 | 4.00 | 4.00 | 0.00 | 30.75 |

The PG ester was polyaldo 10-L-1 Decaglyceryl Monostearate manufactures by Lonza Corp.

Each of these compositions was diluted 1 oz/gallon with OECD hard water and evaluated for microbial efficacy against *Pseudomonas aeruginosa* using the Quantitative Method for evaluations bactericidal activity of microbiocides used on hard, non-porous surfaces (OECD) as outlined previously.

| | ppm in final solution following dilution | | | | |
|---|---|---|---|---|---|
| | QAC (MB50) | PHMB | FMB-AO8 | EDTA | PG Ester |
| 17 | 1000 | 312 | 0 | 0 | 0 |
| 18 | 1000 | 312 | 250 | 1000 | 0 |
| 19 | 1000 | 312 | 500 | 1000 | 0 |
| 20 | 1000 | 312 | 1000 | 1000 | 0 |
| 21 | 1000 | 312 | 2000 | 1000 | 0 |
| 22 | 1953 | 312 | 0 | 0 | 0 |
| 23 | 1000 | 312 | 500 | 1000 | 500 |
| 24 | 1000 | 312 | 500 | 500 | 0 |

| Culture #s | | |
|---|---|---|
| Test System | CFU/mL | Ave CFU/mL |
| *P. aeruginosa* | 265, 304 × $10^7$ | 2.8 × $10^9$ |

| Number Controls | | | | | |
|---|---|---|---|---|---|
| Test System | C1 | C2 | C3 | C4 | Ave CFU/mL |
| *P. aeruginosa* | 156 × $10^9$ | 186 × $10^9$ | 244 × $10^4$ | 277 × $10^4$ | 2.2 × $10^6$ |

| | | | | | Log 6.34 | |
|---|---|---|---|---|---|---|
| Sample | Replicate | CFU/Carrier | Ave CFU/Carrier | Log | Log Reduction | % Reduction |
| 17 | 1 | 64 × $10^3$ | 5.6 × $10^4$ | 4.74 | 1.60 | 97.45 |
| | 2 | 405 × $10^1$ | | | | |
| | 3 | 146 × $10^1$ | | | | |
| 18 | 1 | 89 × $10^1$ | 3.6 × $10^2$ | 2.55 | 3.79 | 99.98 |
| | 2 | 19 × $10^1$ | | | | |
| | 3 | 0(0) | | | | |
| 19 | 1 | 69 × $10^1$ | 3.1 × $10^2$ | 2.49 | 3.85 | 99.98 |
| | 2 | 23 × $10^1$ | | | | |
| | 3 | 0(0) | | | | |
| 20 | 1 | 76(0) | 3.4 × $10^1$ | 1.53 | 4.81 | 99.998 |
| | 2 | 25(0) | | | | |
| | 3 | 1(0) | | | | |
| 21 | 1 | 42(0) | 4.1 × $10^2$ | 2.61 | 3.73 | 99.98 |
| | 2 | 36 × $10^1$ | | | | |
| | 3 | 82 × $10^1$ | | | | |
| 22 | 1 | 14 × $10^3$ | 1.0 × $10^4$ | 4.00 | 2.34 | 99.5 |
| | 2 | 10 × $10^3$ | | | | |
| | 3 | 6 × $10^3$ | | | | |
| 23 | 1 | 5 × $10^3$ | 7.3 × $10^3$ | 3.86 | 2.48 | 99.6 |
| | 2 | 7 × $10^3$ | | | | |
| | 3 | 10 × $10^3$ | | | | |
| 24 | 1 | 9 × $10^3$ | 1.1 × $10^4$ | 4.04 | 2.30 | 99.5 |
| | 2 | 8 × $10^3$ | | | | |
| | 3 | 16 × $10^3$ | | | | |

The results from experiments 17-24 highlight synergy between amine oxide and EDTA in conjunction with PHMB and QAC (see #17 vs. #22, #23 and #24)

Example 13

Evaluates the Impact of Surfactant and Chelant on the Persistent Antimicrobial Effects The test method is based on the EPA method for testing dried chemical residues on hard, non-porous surfaces (modified).
Test Substances: TS3 @ 0.25 oz/gal, 0.5 oz/gal and 1.0 oz/gal.
TS4 @ 0.25 oz/gal, 0.5 oz/gal and 1.0 oz/gal.

| TS3 |
| --- |
| 50% Bardac 205M |
| 20% Vantocil P |
| 30% Distilled water |

| TS4 |
| --- |
| 50% Bardac 205M |
| 20% Vantocil P |
| 6% Lutensol TDA-9 |
| 8% Trilon M |
| 16% Water |

Test Substance Diluent: 400 ppm hard water
Dilutions: 1.0 oz/gal.
  1/128=0.00781×100 mL=0.781.
  0.00781×150 mL=1.17 g/150 mL.
  0.5 oz/gal solution was made by diluting 50 g of 1 oz/gal with 50 g of hard water.
  0.25 oz/gal solution was made by diluting 50 g of 1 oz/gal with 50 g hard water.
Test System: (18-24 hr. AOAC NB) *Pseudomonas aeruginosa* ATCC 15442.
  Prep—decant culture—not disturbing pellicle, vortex and then centrifuge at 10,000 g for 15 minutes and re-suspended in 10 mL PBS.
Organic Soil Load: 5% fetal bovine serum
Carriers: 1"×1" glass microscope slides
Test Substance Application: 50 mL of the test substance was spot inoculated over the carrier in as many spots as possible. The carriers were allowed to dry for 24 hours in disposable Petri dishes in the bio-safety hood/turned off with the lids cracked.
Wears: The test surfaces were subjected to 30 abrasive wears using a dry cloth on the gardner abrasion tested per the EPA methodology. This was immediately followed by Application of a 10 uL bacterial inoculum to the carrier surface. After 10 minutes the carrier was neutralized and any survivors were counted.
Neutralizers: 20 mL DE broth
Dilutions Plated: Inoculation $10^6$ and $10^7$ in duplicate.
Test Carriers: Direct, $10^2$ and $10^4$ in duplicate.
Control Carriers: Direct, $10^2$, $10^3$, and $10^4$ in duplicate.
Plating Medium: Tryptone Glucose Extract Agar
Incubation: 35+/−° C. for 48 hours

| Culture Nos. | | |
| --- | --- | --- |
| Test System | CFU/mL | Ave CFU/mL |
| *P. aeruginosa* | 118 and 122 × $10^7$ | 1.2 × $10^9$ |

| Control Carriers Numbers | | | | | | |
| --- | --- | --- | --- | --- | --- | --- |
| Test System | Wears | Replicate | CFU/mL | CFU/Carrier (×20) | Log | Ave |
| *P. aeruginosa* | 30 | 1 | 164, 136 × $10^3$ | 3.0 × $10^6$ | 6.47 | 6.46 |
|  |  | 2 | 162, 127 × $10^3$ | 2.9 × $10^6$ | 6.46 |  |

| Test Carriers-TS3 | | | | | | | |
| --- | --- | --- | --- | --- | --- | --- | --- |
| Test Substance | Wear | Replicate | Conc. | CFU/mL | CFU/Carrier (×20) | Log Ave | Log Reduction |
| *P. aeruginosa* | 30 | 1 | 0.25 oz/gal | 5, 5 (0) | 1.0 × $10^2$ | 2.21 | 4.25 |
|  |  | 2 |  | 13, 14 (0) | 2.7 × $10^2$ |  |  |
| *P. aeruginosa* | 30 | 1 | 0.5 oz/gal | 1, 0 (0) | <20 | <1.57 | >4.89 |
|  |  | 2 |  | 4, 3 (0) | 7.0 × $10^1$ |  |  |
| *P. aeruginosa* | 30 | 1 | 1.0 oz/gal | 0, 0 (0) | <20 | <1.30 | >5.16 |
|  |  | 2 |  | 1, 0 (0) | <20 |  |  |

| Test Carriers-TS4 | | | | | | | |
| --- | --- | --- | --- | --- | --- | --- | --- |
| Test Substance | Wear | Replicate | Conc. | CFU/mL | CFU/Carrier (×20) | Log Ave | Log Reduction |
| *P. aeruginosa* | 30 | 1 | 0.25 oz/gal | 324, 303 (0) 4, 2 × $10^2$ | 6.1 × $10^3$ | 4.29 | 2.17 |
|  |  | 2 |  | 25, 39 × $10^2$ | 6.4 × $10^4$ |  |  |

-continued

| Test Carriers-TS4 | | | | | | | |
|---|---|---|---|---|---|---|---|
| Test Substance | Wear | Replicate | Conc. | CFU/mL | CFU/Carrier (×20) | Log Ave | Log Reduction |
| P. aeruginosa | 30 | 1 | 0.5 oz/gal | 142, 146 (0) | $2.9 \times 10^3$ | 4.00 | 2.46 |
|  |  | 2 |  | 18, 18 × $10^2$ | $3.6 \times 10^4$ |  |  |
| P. aeruginosa | 30 | 1 | 1.0 oz/gal | 9, 10 (0) | $1.9 \times 10^2$ | 3.37 | 3.09 |
|  |  | 2 |  | 15, 15 × $10^2$ | $3.0 \times 10^4$ |  |  |

The comparison of TS3 to TS4 provides 2 key pieces of information. It first highlights the lower limits of PHMB and QAC where we are still able to achieve at least a 4 log reduction following abrasive wear (e.g. TS3 diluted 0.25 oz/gallon ~975 ppm QAC and ~156 ppm PHMB)

However when testing the TS4 composition (inclusive of the lutensol TDA-9 surfactant and Trilon M builder) the residual efficacy is markedly reduced relative to the actives alone. This highlights the negative impact that surfactant and chelant choice and levels can have on residual efficacy.

Example 14

Once critical levels of active and negative effects of builder were determined we took the next step of evaluating the system with the best "wet" for residual efficacy relative to the example containing TDA and Trilon as outlined in examples 10 and 13.

Our focus was on the mixture of QAC, PHMB, AO-8 and EDTA.

| Formulations | | | |
|---|---|---|---|
|  | MB50 | PHMB | EDTA Conc (ppm) | AO-8 conc (ppm) |
| 12837-42.1 | 3900 | 625 | 0 | 0 |
| 12837-42.2 | 3900 | 625 | 0 | 500 |

-continued

| Formulations | | | | |
|---|---|---|---|---|
|  | MB50 | PHMB | EDTA Conc (ppm) | AO-8 conc (ppm) |
| 12837-42.3 | 3900 | 625 | 0 | 1000 |
| 12837-42.4 | 3900 | 625 | 500 | 0 |
| 12837-42.5 | 3900 | 625 | 500 | 500 |
| 12837-42.6 | 3900 | 625 | 500 | 1000 |
| 12837-42.7 | 3900 | 625 | 1000 | 0 |
| 12837-42.8 | 3900 | 625 | 1000 | 500 |
| 12837-42.9 | 3900 | 625 | 1000 | 1000 |

These solutions were testing using the same procedure as outlined in Example #13.

| Culture Nos. | |
|---|---|
| Test System | CFU/mL |
| P. aeruginosa | 90, 82 × $10^7$ |
|  | 5:1 152, 160 × $10^6$ |

| Control Carriers | | | | | | |
|---|---|---|---|---|---|---|
| Test System | Wear | Replicate | CFU/mL | CFU/Carrier (×20) | Log | Ave |
| P. aeruginosa | 30 | 1 | 119, 173 × $10^3$ | $2.9 \times 10^6$ | 6.46 | 6.45 |
|  |  | 2 | 123, 156 × $10^3$ | $2.8 \times 10$ | 6.44 |  |

| Test Substance | Wear | Replicate | CFU/mL | CFU/Carrier (×20) | Log | Ave | Log Reduction |
|---|---|---|---|---|---|---|---|
| 12837-42.1 | 30 | 1 | 1, 1 (0) | 20 | 1.30 | 1.45 | 5.00 |
|  |  | 2 | 2, 0 (0) | 40 | 1.60 |  |  |
| 12837-42.2 | 30 | 1 | 0, 0 (0) | <20 | <1.30 | <1.30 | >5.15 |
|  |  | 2 | 0, 0 (0) | <20 | <1.30 |  |  |
| 12837-42.3 | 30 | 1 | 0, 0 (0) | <20 | <1.30 | <1.65 | >4.80 |
|  |  | 2 | 5, 5 (0) | $1 \times 10^2$ | 2.00 |  |  |
| 12837-42.4 | 30 | 1 | 1, 1 (0) | 20 | 1.30 | <1.30 | 5.15 |
|  |  | 2 | 0, 0 (0) | <20 | <1.30 |  |  |
| 12837-42.5 | 30 | 1 | 14, 11 (0) | $2.4 \times 10^2$ | 2.38 | 2.59 | 3.86 |
|  |  | 2 | 30, 35 (0) | $6.5 \times 10^2$ | 2.81 |  |  |
| 12837-42.6 | 30 | 1 | 167, 175 (0) | $3.4 \times 10^3$ | 3.53 | 2.56 | 3.89 |
|  |  | 2 | 2, 1 (0) | 40 | 1.60 |  |  |
| 12837-42.7 | 30 | 1 | 0, 0 (0) | <20 | <1.30 | <1.45 | >5.00 |
|  |  | 2 | 2, 0 (0) | 40 | 1.60 |  |  |
| 12837-42.8 | 30 | 1 | 6, 3 (0) | 80 | 1.90 | 2.10 | 4.35 |
|  |  | 2 | 15, 5 (0) | $2 \times 10^2$ | 2.30 |  |  |
| 12837-42.9 | 30 | 1 | 6, 6 (0) | $1.2 \times 10^2$ | 2.07 | 2.77 | 3.68 |
|  |  | 2 | 156, 147 (0) | $3.0 \times 10^3$ | 3.47 |  |  |

Result summary

|   | QAC/PHMB (ppm) | EDTA Conc (ppm) | AO-8 conc (ppm) | Log reduction |
|---|---|---|---|---|
| 1 | 3900/625 | 0 | 0 | 5.00 |
| 2 | 3900/625 | 0 | 500 | >5.15 |
| 3 | 3900/625 | 0 | 1000 | >4.80 |
| 4 | 3900/625 | 500 | 0 | >5.15 |
| 5 | 3900/625 | 500 | 500 | 3.86 |
| 6 | 3900/625 | 500 | 1000 | 3.89 |
| 7 | 3900/625 | 1000 | 0 | >5.00 |
| 8 | 3900/625 | 1000 | 500 | 4.35 |
| 9 | 3900/625 | 1000 | 1000 | 3.68 |

These results were markedly superior to the composition from example #13 based on Lutensol and Trilon M. But surprisingly, the experiment indicated that the combination of EDTA with AO-8 provided less residual efficacy that compositions containing those materials individually (See #2, 3, 4 and #7).

Example 15

To understand the results from experiment #14 we ran an additional experiment using this same methodology with one critical difference. In this experiment we compared the efficacy of a treated carrier inoculated with 10 uL of bacterial inoculum vs. one treated with 10 uL of inoculum with 40 uL of added water making the total inoculum volume 50 uL. The net effect of this was a 5× dilution of the chemistry on the surface of the treated carrier.

This test is driven by the standard methodology. The normal test method calls for addition of 50 uL of chemistry to our 1"×1" carrier. That chemistry is dried and subsequently abraded to remove a portion of the chemistry from that surface (simulating wear that would occur if a treated surface were touched many times). This worn surface is then inoculated with 10 uL of a bacterial suspension where it reacts on that surface for 10 minutes. The critical factor here is the addition of 10 uL of inoculum to the dried residue of 50 uL of chemistry.

Because of this when the inoculum re-hydrates the chemical residue it represents as much as a 5× increase in the concentration of actives. The solutions in example #13 and #14 indicate that both AO-8, EDTA and Lutensol TDA-9 have a detrimental effect on the residual efficacy of PHMB/QAC during this concentration effect. Though AO-8 is less affected than TDA9 making selection of that ingredient more appropriate for a mixture that provides both good "wet" and "dry' residual activity.

That said an experiment where we re-hydrate our chemistry with 50 uL vs. 10 uL helps us both understand the mechanism and defines lower limits of chemistry where acceptable efficacy can be found. The test composition we chose for this experiment is outlined below.

Test composition:

|  | MB50 | PHMB | EDTA Conc (ppm) | AO-8 conc (ppm) |
|---|---|---|---|---|
| 13137.9.1 | 3900 | 625 | 1000 | 1000 |

This solution was dried onto a carrier and challenged with 10 uL or 50 uL of bacterial inoculum with the results outlined below

| Test Substance | Wear | Replicate | CFU/mL | CFU/Carrier (×20) | Log | Ave | Log Reduction |
|---|---|---|---|---|---|---|---|
| 13137-9.1 10 ul inoculum | 30 | 1 | 66, 63 (0) | $1.3 \times 10^3$ | 3.11 | 2.62 | 3.86 |
|  |  | 2 | 8, 6 (0) | $1.4 \times 10^2$ | 2.14 |  |  |
| 13137-9.1 50 uL inoculum | 30 | 1 | 0, 0 (0) | <20 | <1.30 | <1.30 | >5.15 |
|  |  | 2 | 0, 0 (0) | <20 | <1.30 |  |  |

Example 16

Because disinfectants are used in a variety of different areas it is critical to develop compositions that are minimally irritating to the workers who use them as part of their daily routine. One area of particular concern is the potential eye irritancy of a disinfectant composition. This becomes particularly important when we look at a product that is intended to provide a semi-durable residue on disinfected surfaces as that may require higher levels of active ingredients than would be required for a conventional disinfectant.

As part of our development process we discovered that we could achieve very effect "wet" and "dry" residual efficacy with a range of compositions. But as the development progressed it became clear that there was a range of ingredients and concentration ranges that were preferred due to their low irritancy.

Compositions:

| Raw Material | 12837.39.1 | 12837.39.2. | 12837.39.3. | 12837.36.1 |
|---|---|---|---|---|
| Water (DT) | 6 g | 23 g | 23 g | 23 g |
| Luntensol TDA-9 |  |  |  | 6 g |
| Lonza MB-50 | 50 g | 25 g | — | — |
| Lonza 205M | — | — | 25 g | 50 g |
| Vantocil P | 20 g | 20 g | 20 g | 20 g |
| Lonza AO-8 | 8 g | 16 g | 16 g | — |
| Versene 100 | 16 g | 16 g | 16 g | — |
| Trilon M | — | — | — | 16 g |

Each of these compositions was diluted at a rate of 2 oz/gal before they were tested using the Epiocular model.

Methodology:

The MatTek EpiOcular™ model can be used to assess the potential ocular irritation of test articles by determining the cell viability of the tissue after exposure to the test articles. The objective of this study was to assess the ocular irritation potential of 1.56% (w/w) 12837.36.1. Control and test article exposure times were 5 minutes, 10 minutes, 20 minutes, 40 minutes and 60 minutes. After the exposures MTT was performed and data was normalized to the negative control, sterile ultrapure water (water purified and deionized ~18.2 MΩ-cm). The positive control, 10% benzalkonium chloride (BC), was effective, reducing cell viability to <10% of control for all exposure times (Tables 2a-e) and FIG. 1). The relative cell viability of ocular tissues treated with 1.56% (w/w) 12837.36.1 was 29.7%, 26.8%, 15.3%, 8.9% and 8.0% after 5, 10, 20, 40 and 60 minute exposures, respectively (Tables 2a-e and FIG. 1), resulting in an $ET_{50}$ of 1.54 minutes and an estimated in vivo Draize score of 77.2 (Table 1). Because of the results of this study, 1.56% (w/w) 12837.36.1 was categorized as a severe/extreme ocular irritant.

TABLE 1

Ocular Irritancy categorization.

| | $ET_{50}$ (min) | Estimated Draize | Categorization |
|---|---|---|---|
| 10% Benzalkonium Cl | 0.03 | >110 | Severe/Extreme Irritant |
| 1.56% (w/w) 12837.36.1 | 1.54 | 77.2 | Severe/Extreme Irritant |

The MatTek EipOcular™ model can be used to assess the potential ocular irritation of test articles by determining the cell viability of the tissue after exposure to the test articles. The objective of this study was to assess the ocular irritation potential of 1.56% (w/w) 12837.39.1. Control and test article exposure times were 5 minutes, 10 minutes, 20 minutes, 40 minutes and 60 minutes. After the exposures MTT was performed and data was normalized to the negative control, sterile ultrapure water (water purified and deionized ~18.2 MΩ-cm). The positive control, 10% benzalkonium chloride (BC), was effective, reducing cell viability to <10% of control for all exposure times (Tables 2a-e) and FIG. 1). The relative cell viability of ocular tissues treated with 1.56% (w/w) 12837.39.1 was 87.5%, 48.8%, 32.9%, 17.3% and 12.8% after 5, 10, 20, 40 and 60 minute exposures, respectively (Tables 2a-e and FIG. 1), resulting in an $ET_{50}$ of 9.24 minutes and an estimated in vivo Draize score of 28.7 (Table 1). Because of the results of this study, 1.56% (w/w) 12837.39.1 was categorized as a moderate ocular irritant.

TABLE 1

Ocular Irritancy categorization

| | $ET_{50}$ (min) | Estimated Draize | Categorization |
|---|---|---|---|
| 10% Benzalkonium Cl | 0.03 | >110 | Severe/Extreme Irritant |
| 1.56% (w/w) 12837.39.1 | 9.24 | 28.7 | Moderate Irritant |

The MatTek EipOcular™ model can be used to assess the potential ocular irritation of test articles by determining the cell viability of the tissue after exposure to the test articles. The objective of this study was to assess the ocular irritation potential of 1.56% (w/w) 12837.39.2. Control and test article exposure times were 5 minutes, 10 minutes, 20 minutes, 40 minutes and 60 minutes. After the exposures MTT was performed and data was normalized to the negative control, sterile ultrapure water (water purified and deionized ~18.2 MΩ-cm). The positive control, 10% benzalkonium chloride (BC), was effective, reducing cell viability to <10% of control for all exposure times (Tables 2a-e) and FIG. 1). The relative cell viability of ocular tissues treated with 1.56% (w/w) 12837.39.2 was 103.5%, 90.2%, 75.1%, 45.0% and 19.7% after 5, 10, 20, 40 and 60 minute exposures, respectively (Tables 2a-e and FIG. 1), resulting in an $ET_{50}$ of 36.43 minutes and an estimated in vivo Draize score of 12.1 (Table 1). Because of the results of this study, 1.56% (w/w) 12837.39.2 was categorized as a minimal to non-ocular irritant.

TABLE 1

Ocular Irritancy categorization

| | $ET_{50}$ (min) | Estimated Draize | Categorization |
|---|---|---|---|
| 10% Benzalkonium Cl | 0.03 | >110 | Severe/Extreme Irritant |
| 1.56% (w/w) 12837.39.2 | 36.43 | 12.1 | Minimal to Non-Irritant |

The MatTek EpiOcular™ model can be used to assess the potential ocular irritation of test articles by determining the cell viability of the tissue after exposure to the test articles. The objective of this study was to assess the ocular irritation potential of 1.56% (w/w) 12837.39.3. Control and test article exposure times were 5 minutes, 10 minutes, 20 minutes, 40 minutes and 60 minutes. After the exposures MTT was performed and data was normalized to the negative control, sterile ultrapure water (water purified and deionized ~18.2 MΩ-cm). The positive control, 10% benzalkonium chloride (BC), was effective, reducing cell viability to <10% of control for all exposure times (Tables 2a-e) and FIG. 1). The relative cell viability of ocular tissues treated with 1.56% (w/w) 12837.39.3 was 69.6%, 73.5%, 62.5%, 25.3% and 17.2% after 5, 10, 20, 40 and 60 minute exposures, respectively (Tables 2a-e and FIG. 1), resulting in an $ET_{50}$ of 23.36 minutes and an estimated in vivo Draize score of 12.1 (Table 1). Because of the results of this study, 1.56% (w/w) 12837.39.3 was categorized as a mild ocular irritant.

TABLE 1

Ocular Irritancy categorization

| | $ET_{50}$ (min) | Estimated Draize | Categorization |
|---|---|---|---|
| 10% Benzalkonium Cl | 0.03 | >110 | Severe/Extreme Irritant |
| 1.56% (w/w) 12837.39.3 | 23.36 | 16.3 | Mild Irritant |

Conclusion:

To be defined as a sanitizer, the test substances on the hard inanimate surface must reduce the total number of organisms by at least 99.9% (based on the Geometric Mean) on the surface within a 5 minute period (after the final inoculation).

The antimicrobial efficacy of the commercial disinfectant dropped off with continual wearing of the treated surface. After 10 and 20 wears, a greater than 99.9% reduction in S. aureus numbers were observed, but fell below acceptable levels over 20 wears.

The antimicrobial efficacy of the QAC blend alone showed variable results. QAC showed some efficacy with all wear cycles, but a greater than 99.9% reduction in S. aureus numbers was only observed with the 30 wear testing.

The antimicrobial efficacy of the PHMB alone showed little to no efficacy again S. aureus with any of the wear cycles tested.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

What is claimed is:

1. A method of disinfecting a surface comprising: diluting a concentrated anti-microbial composition to form a use solution, wherein said composition comprises from about 5 wt. % to about 50 wt. % of a quaternary ammonium compound; from about 1 wt. % to about 8 wt. % of a cationic biocide; an amine oxide surfactant; and a chelant, wherein the ratio of quaternary ammonium to surfactant is from about 2:1 to about 7:1 on a weight basis, and wherein the ratio of the quaternary ammonium to cationic biocide is from about 10:1 to about 0.5:1 by weight; wherein the concentrated anti-microbial composition is diluted with water or an aqueous dilutent in a ratio from about 1:10 to about 1:500 so that between about 195 ppm to about 7800 ppm of the quaternary ammonium compound and about 19.5 ppm to about 1250 ppm of the cationic biocide are present in the use solution: wherein the concentrated anti-microbial composition is free of citrate salts; and applying the use solution to a surface, wherein the use solution cleans said surface by providing wet kill; and generates a protective coating and a film that continues to reduce microbial contamination.

2. A method according to claim 1, wherein the film provides a 99% reduction of *Pseudomonas aeruginosa* and *Staphylococcus aureus* following 30 abrasive wear cycles.

3. The method of claim 1, wherein the use solution provides no eye irritancy.

4. The method of claim 1, wherein said use solution provides wet and dry efficacy.

5. The method of claim 1, wherein said use solution of the anti-microbial composition provides no eye irritancy, with wet and dry efficacy and reduction in microbial contamination.

6. The method of claim 1, wherein said use solution of the anti-microbial composition provides 99.9% log reduction in microbial contamination.

* * * * *

UNITED STATES PATENT AND TRADEMARK OFFICE
CERTIFICATE OF CORRECTION

PATENT NO. : 10,912,299 B2
APPLICATION NO. : 14/864437
DATED : February 9, 2021
INVENTOR(S) : Brandon Herdt et al.

Page 1 of 1

It is certified that error appears in the above-identified patent and that said Letters Patent is hereby corrected as shown below:

In the Claims

<u>In Column 74, Claim 1, Line 3:</u>
DELETE "dilutent" after "aqueous"
Insert --diluent-- after "aqueous"

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*